US008173662B2

(12) United States Patent
Evans et al.

(10) Patent No.: US 8,173,662 B2
(45) Date of Patent: May 8, 2012

(54) FUSED PYRIMIDINES AS INHIBITORS OF NUCLEOSIDE PHOSPHORYLASES AND NUCLEOSIDASES

(75) Inventors: Gary Brian Evans, Lower Hutt (NZ); Richard Hubert Furneaux, Wilton (NZ); Dirk Henning Lenz, Wellington (NZ); Vern L. Schramm, New Rochelle, NY (US); Peter Charles Tyler, Northland (NZ); Olga Vladimirovna Zubkova, Wellington (NZ)

(73) Assignees: Industrial Research Limited, Auckland (NZ); Albert Einstein College of Medicine of Yeshiva University, Bronx, NY (US)

( * ) Notice: Subject to any disclaimer, the term of this patent is extended or adjusted under 35 U.S.C. 154(b) by 377 days.

(21) Appl. No.: 12/455,537

(22) Filed: Jun. 3, 2009

(65) Prior Publication Data

US 2009/0239885 A1 Sep. 24, 2009

Related U.S. Application Data

(62) Division of application No. 10/524,995, filed as application No. PCT/NZ2003/000186 on Aug. 21, 2003, now Pat. No. 7,553,839.

(30) Foreign Application Priority Data

Aug. 21, 2002 (NZ) ........................... 520919

(51) Int. Cl.
  C07D 487/04 (2006.01)
  A61K 31/519 (2006.01)
  A61P 35/04 (2006.01)
  A61P 31/04 (2006.01)
  A61P 37/06 (2006.01)
  A61P 33/02 (2006.01)

(52) U.S. Cl. ............ 514/262.1; 544/262; 544/280; 514/265.1

(58) Field of Classification Search ............ 544/262; 514/262.1
See application file for complete search history.

(56) References Cited

U.S. PATENT DOCUMENTS

| 5,744,475 | A | 4/1998 | Yano et al. |
|---|---|---|---|
| 5,985,848 | A | 11/1999 | Furneaux et al. |
| 6,066,722 | A | 5/2000 | Furneaux et al. |
| 6,228,847 | B1 | 5/2001 | Furneaux et al. |
| 6,379,911 | B2 | 4/2002 | Furneaux et al. |
| 6,458,799 | B1 | 10/2002 | Montgomery et al. |
| 6,492,347 | B2 | 12/2002 | Furneaux et al. |
| 6,596,720 | B1 | 7/2003 | Hoshino et al. |
| 6,693,193 | B1 | 2/2004 | Furneaux et al. |
| 6,764,829 | B2 | 7/2004 | Schramm et al. |
| 6,803,455 | B2 | 10/2004 | Furneaux et al. |
| 7,022,852 | B2 | 4/2006 | Furneaux et al. |
| 7,098,334 | B2 | 8/2006 | Furneaux et al. |
| 7,109,331 | B2 | 9/2006 | Furneaux et al. |
| 7,211,653 | B2 | 5/2007 | Furneaux et al. |
| 7,211,677 | B2 | 5/2007 | Furneaux et al. |
| 7,390,890 | B2 | 6/2008 | Furneaux et al. |
| 7,405,297 | B2 | 7/2008 | Furneaux et al. |
| 7,553,839 | B2 | 6/2009 | Evans et al. |
| 7,655,795 | B2 | 2/2010 | Evans et al. |
| 2006/0217551 | A1 | 9/2006 | Evans et al. |
| 2008/0280334 | A1 | 11/2008 | Lenz et al. |
| 2009/0233948 | A1 | 9/2009 | Evans et al. |
| 2009/0325986 | A1 | 12/2009 | Furneaux et al. |
| 2010/0062995 | A1 | 3/2010 | Schramm |
| 2010/0094003 | A1 | 4/2010 | Evans et al. |
| 2010/0168141 | A1 | 7/2010 | Evans et al. |
| 2010/0222370 | A1 | 9/2010 | Schramm et al. |
| 2011/0046167 | A1 | 2/2011 | Clinch et al. |

FOREIGN PATENT DOCUMENTS

| EP | 0763529 B1 | 7/2003 |
|---|---|---|
| EP | 1230925 B1 | 8/2005 |
| WO | WO 99/19338 | 4/1999 |
| WO | WO 02/18371 A1 | 3/2002 |
| WO | WO 2005/118532 | 12/2005 |
| WO | WO 2006/014913 A2 | 2/2006 |
| WO | WO 2006/123953 A1 | 11/2006 |
| WO | 2007016291 A2 | 2/2007 |
| WO | WO 2007/069923 A1 | 6/2007 |
| WO | 2007097648 A1 | 8/2007 |
| WO | WO 2007/097647 A1 | 8/2007 |
| WO | WO 2007/097648 A1 | 8/2007 |
| WO | 2008030119 A1 | 3/2008 |
| WO | 2009082247 A1 | 7/2009 |
| WO | 2010033236 A2 | 2/2010 |
| WO | 2011008110 A1 | 1/2011 |

OTHER PUBLICATIONS

Supplementary European Search Report dated Apr. 16, 2010 in connection with EP Patent Application No. 03792904.9, 2 pages.
Brakta M et al, entitled "Efficient Synthesis of 3H,5H-Pyrrolo[3,2-d]pyrimidin-4-one," J. Chem. Soc. Perkin Trans., 1992, vol. 1, pp. 1883-1884.
Evans G B et al. "Synthesis of a transition state analogue inhibitor of purine nucleoside phosphorylase via the Mannich reaction," Organic Letters 2003, 5(20), 3639-3640. Filichev V V et al., entitled "Synthesis of 1'-aza-C-nucleosides from (3R,4R)-4-(hydroxymethyl)pyrrolidin-3-ol," Tetrahedron 57 (2001) 9163-9168.
Galeazzi, R et al., "Chiral 3-hydroxypyrrolidin-2-ones from a Baylis-Hillman adduct: convergent, stereoselective synthesis of glycosidase inhibitor," Tetrahedron: Asymmetry, vol. 15, pp. 3249-3256.

(Continued)

*Primary Examiner* — Susanna Moore

(74) *Attorney, Agent, or Firm* — Amster, Rothstein & Ebenstein LLP

(57) ABSTRACT

The present invention relates to compounds of the general formula (I) which are inhibitors of purine muclioside phosphorylases (PNP), purine phosphoribosyltransferases (PPRT), 5'-methylthioadenosine phosphorylases (MTAP), 5'-methylthioadenosine mucliosidases (MTAN) and/or nucleoside hydrolases (NH). The invention also relates to the use of these compounds in the treatment of diseases and infections including cancer, bacterial infections, protozoal infections, and T-cell mediated disease and to pharmaceutical compositions containing the compounds.

20 Claims, 2 Drawing Sheets

OTHER PUBLICATIONS

Kamath V P et al., entitled "Synthesis of a potent transition-state inhibitor of 5'-Deoxy-5'-methylthioadenosine phosphorylase," J. Med. Chem. 2004, 47, 1322-1324.

Kametani, T et al., "Studies on the Syntheses of Heterocylic Compounds. 762. Synthesis of 3-benzyl-6-methyl-2-oxo-3,6-diazabicyclo[3.1.0]hexane as a synthetic intermediate of mitomycins," Tetrahedron, 1979, 35(3), pp. 313-316.

Karlsson S et al., entitled "Synthesis of enantiomerically pure 4-substituted pyrrolidin-3-ols via asymmetric 1,3-dipolar cycloaddition," Tetrahedron: Asymmetry 12 (2001) 1977-1982.

International Searching Authority, "Written Opinion of the International Searching Authority," for International Application No. PCT/NZ2004/000017, 3 pages.

"International Preliminary Report on Patentability," for International Application No. PCT/NZ2004/000017, 3 pages.

"International Preliminary Examination Report," for International Application No. PCT/NZ2003/000186, 3 pages.

Lewandowicz A et al., entitled "Energetic Mapping of Transition State Analogue Internations with Human and *Plasmodium falciparum* Purine Nucleotide Phosphorylases" Journal of Biological Chemistry, 2005, 280(34), 30320-30328.

Lim M-I et al., entitled "A New Synthesis of Pyrrolo[3,2-d]pyrimidines ("9-Deazapurines") via 3-Amino-2-carboalkoxypyrroles," J. Org. Chem., 1979, vol. 44, No. 22, pp. 3826-3829.

Miles R W et al., entitled "One-Third-the-Sites Transition-State Inhibitors for Purine Nucleoside Phosphorylase," Biochemistry, 1998, vol. 37, No. 24, pp. 6-12.

STN File CA abstract No. 91-123648 (4 pages).

Wolff M E, entitled "Some Considerations for Prodrug Design,"Burger's Medicinal Chemistry and Drug Discovery, 5ed, vol. 1, 1995, pp. 975-977.

Taylor E C et al., entitled "An Expeditious Synthesis of 2-Amino-4(3H)-oxo-5H-pyrrolo [3,2-d]pyrimidine (9-Deazaguanine)," Tetrahedron Letters, 1993, vol. 34, No. 29, pp. 4595-4598.

Banker G S et al., Modern Pharmaceutics, 3ed., 1996, pp. 451, 596.

Anonymous, BioCryst News., <http://shareholder.com/biocryst/news/19980429-25543cfm?ReleaseID=25543>, Apr. 29, 2998.

Evans G.B. et al., "Exploring Structure-Activity Relationships of Transition State Analogues of Human Purine Nucleoside Phosphorylase." Journal of Medicinal Chemistry, 46:3412-3423, 2003.

Lewansowicz A. et al., "Over-the-Barrier Transition State Analogues and Crystal Structure with *Mycobacterium tuberculosis* Purine Nucleoside Phosphorylase." Biochemistry, 42:6057-6066, 2003.

FUSED PYRIMIDINES AS INHIBITORS OF NUCLEOSIDE PHOSPHORYLASES AND NUCLEOSIDASES

CROSS-REFERENCE TO RELATED APPLICATIONS

This application is a divisional of U.S. patent application Ser. No. 10/524,995, filed Sep. 27, 2005, now U.S. Pat. No. 7,553,839, which is a U.S. National Phase of PCT Application No. PCT/NZ2003/000186, filed Aug. 21, 2003, and claims priority to New Zealand Application No. 520919, filed Aug. 21, 2002, the contents of which are herein incorporated by reference.

STATEMENT OF GOVERNMENT SUPPORT

This invention was made with U.S. Government support under grant number GM41916 awarded by the National Institutes of Health, U.S. Department of Health and Human Services. The U.S. Government has certain rights in the invention.

TECHNICAL FIELD

This invention relates to certain nucleoside analogues which are inhibitors of PNP, PPRT, MTAP, MTAN, and/or NH, the use of these compounds as pharmaceuticals and pharmaceutical compositions containing the compounds. The invention also relates to methods of treating diseases.

BACKGROUND

U.S. Pat. No. 5,985,848, U.S. Pat. No. 6,066,722 and U.S. Pat. No. 6,228,741 are directed to nucleoside analogues that are inhibitors of purine nucleoside phosphorylase (PNP) and purine phosphoribosyltransferases (PPRT). The analogues are useful in treating parasitic infections, T-cell malignancies, autoimmune diseases and inflammatory disorders. The analogues are also useful for immunosuppression in organ transplantation.

PCT/NZ00/00048 provides a process for preparing certain PNP inhibitor compounds. This application recognises the compounds as PNP inhibitors and addresses a need for simpler methods of preparing them. PCT/NZ01/00174 also provides further nucleoside analogues that are inhibitors of PNP and PPRT.

Certain nucleoside analogues have also been identified as potent inhibitors of 5'-methylthioadenosine phosphorylase (MTAP) and 5'-methylthioadenosine nucleosidase (MTAN). These are the subject of PCT/NZ03/00050.

The applicants of the present application have also developed a process for preparing methylene linked cyclic amine deazapurines including reacting formaldehyde, or a formaldehyde equivalent, with a cyclic amine and a heteroaromatic compound. This process is the subject of New Zealand patent application no. 523970

PNP catalyses the phosphorolytic cleavage of ribo- and deoxyribonucleosides, for example those of guanine and hypoxanthine, to give the corresponding sugar-1-phosphate and guanine, hypoxanthine or other purine bases.

Humans deficient in purine nucleoside phosphorylase (PNP) suffer a specific T-cell immunodeficiency due to an accumulation of dGTP which prevents proliferation of stimulated T lymphocytes. Inhibitors against PNP are therefore immunosuppressive, and are active against T-cell malignancies and T-cell proliferative disorders.

Nucleoside hydrolases (NH) catalyse the hydrolysis of nucleosides. These enzymes are not found in mammals but are required for nucleoside salvage in some protozoan parasites. Some protozoan parasites use nucleoside phosphorylases either instead of or in addition to, nucleoside hydrolases for this purpose. Inhibitors of nucleoside hydrolases and phosphorylases can be expected to interfere with the metabolism of the parasite and can therefore be usefully employed against protozoan parasites.

MTAP and MTAN function in the polyamine biosynthesis pathway, in purine salvage in mammals, and in the quorum sensing pathways in bacteria. MTAP catalyses the reversible phosphorolysis of 5'-methylthioadenosine (MTA) to adenine and 5-methylthio-$\alpha$-D-ribose-1-phosphate (MTR-1P). MTAN catalyses the reversible hydrolysis of MTA to adenine and 5-methylthio-$\alpha$-D-ribose and of S-adenosyl-L-homocysteine (SAH) to adenine and S-ribosyl-homocysteine (SRH). The adenine formed is subsequently recycled and converted into nucleotides. Essentially, the only source of free adenine in the human cell is a result of the action of these enzymes. The MTR-1P is subsequently converted into methionine by successive enzymatic actions.

MTA is a by-product of the reaction involving the transfer of an aminopropyl group from decarboxylated S-adenosyl-methionine to putrescine during the formation of spermidine. The reaction is catalyzed by spermidine synthase. The spermidine synthase is very sensitive to product inhibition by accumulation of MTA. Therefore, inhibition of MTAP or MTAN severely limits the polyamine biosynthesis and the salvage pathway for adenine in the cells. Likewise, MTA is the by-product of the bacterial synthesis of acylated homoserine lactones from S-adenosylmethionine (SAM) and acyl-acyl carrier proteins in which the subsequent lactonization causes release of MTA and the acylated homoserine lactone. The acylated homoserine lactone is a bacterial quorum sensing molecule in bacteria that is involved in bacterial virulence against human tissues. Recent work has identified a second communication system (autoinducer 2, AI-2) that is common to both Gram-positive and Gram-negative bacteria and thus has been proposed as a "universal signal" which functions in interspecies cell-to-cell-communication. Again, MTAN generates S-ribosyl-homocysteine (SRH) that is the precursor of AI-2. Inhibition of MTAN or MTAP in microbes will prevent MTA removal and subject the pathway to product inhibition, thereby decreasing production of the quorum sensing pathway and decreasing the virulence of microbial infections. Inhibition of MTAN in microbes will prevent the formation of SRH, decreasing the production of the second quorum sensing pathway.

MTAP deficiency due to a genetic deletion has been reported with many malignancies. The loss of MTAP enzyme function in these cells is known to be due to homozygous deletions on chromosome 9 of the closely linked MTAP and p16/MTS1 tumour suppressor gene. As absence of p16/MTS1 is probably responsible for the tumour, the lack of MTAP activity is a consequence of the genetic deletion and is not causative for the cancer. However, the absence of MTAP alters the purine metabolism in these cells so that they are mainly dependent on the de novo pathway for their supply of purines. That makes these cells unusually sensitive to inhibitors like methotrexate, alanosine and azaserine, that block the de novo pathway. Therefore, a combination therapy of methotrexate, alanosine or azaserine with an MTAP inhibitor will have unusually effective anti-tumour properties.

MTAP inhibitors would also be very effective against parasitic infection such as malaria that infects red blood cells (RBCs), as they lack the de novo pathway for purine biosynthesis. Protozoan parasites depend entirely upon the purines produced by the salvage pathway for their growth and propagation. MTAP inhibitors will therefore kill these parasites without having any negative effect on the host RBCs, as RBCs are terminally differentiated cells and they do not synthesize purines, produce polyamines or multiply.

The imino sugar part of the compounds described most of the patent specifications referred to above has the nitrogen atom located between C-1 and C-4 so as to form 1,4-dideoxy-1,4-imino-D-ribitol compounds. The location of the nitrogen atom in the ribitol ring may be critical for binding to enzymes. In addition, the location of the link between the sugar part and the nucleoside base analogue may be critical for enzyme inhibitory activity. The known compounds have that link at C-1 of the sugar ring.

In the search for new and improved nucleoside phosphorylase and nucleosidase inhibitors, the applicants have Investigated the synthesis and bioactivity of compounds where the location of the nitrogen atom in the sugar ring is varied and, additionally, where two nitrogen atoms form part of the sugar ring. Alternative modes of linking the sugar part and the base analogue have also been investigated.

The applicants have surprisingly found that certain novel compounds exhibit potent inhibitory activity against one or more of PNP, PPRT, MTAP and the nucleoside hydrolase MTAN.

It is therefore an object of the present invention to provide a compound that is an inhibitor of PNP, PPRT, MTAP, MTAN, and/or NH or to at least provide a useful choice.

STATEMENTS OF INVENTION

In a first aspect of the invention there is provided a compound of the formula (I):

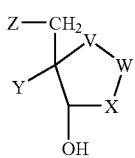

(I)

wherein:
V is selected from $CH_2$ and NH, and W is selected from $NR^1$ and $NR^2$; or V is selected from $NR^1$ and $NR^2$, and W is selected from $CH_2$ and NH;
X is selected from $CH_2$ and CHOH in the R or S-configuration;
Y is selected from hydrogen, halogen and hydroxy, except where V is selected from NH, $NR^1$ and $NR^2$ then Y is hydrogen;
Z is selected from hydrogen, halogen, hydroxy, SQ, OQ and Q, where Q is an optionally substituted alkyl, aralkyl or aryl group;
$R^1$ is a radical of the formula (II)

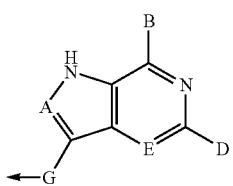

(II)

$R^2$ is a radical of the formula (III)

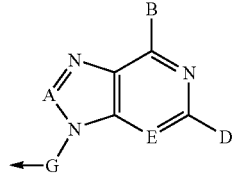

(III)

A is selected from N, CH and CR, where R is selected from halogen, optionally substituted alkyl, aralkyl or aryl, OH, $NH_2$, $NHR^3$, $NR^3R^4$ and $SR^5$, where $R^3$, $R^4$ and $R^5$ are each optionally substituted alkyl, aralkyl or aryl groups;
B is selected from OH, $NH_2$, $NHR^6$, SH, hydrogen and halogen, where $R^6$ is an optionally substituted alkyl, aralkyl or aryl group;
D is selected from OH, $NH_2$, $NHR^7$, hydrogen, halogen and $SCH_3$, where $R^7$ is an optionally substituted alkyl, aralkyl or aryl group;
E is selected from N and CH;
G is selected from $CH_2$ and NH, or G is absent, provided that where W is $NR^1$ or $NR^2$ and G is NH then V is $CH_2$, and provided that where V is $NR^1$ or $NR^2$ and G is NH then W is $CH_2$;
or a tautomer thereof, or a pharmaceutically acceptable salt thereof, or an ester thereof, or a prodrug thereof.

Preferably Z is selected from hydrogen, halogen, hydroxy, SQ and OQ. More preferably Z is OH. Alternatively it is preferred that Z is SQ. In another preferred embodiment, Z is Q.

It is also preferred that V is $CH_2$. It is further preferred that X is $CH_2$. Additionally, it is preferred that G is $CH_2$.

Preferably W is $NR^1$. Alternatively it is preferred that W is $NR^2$. It is also preferred that where W is selected from NH, $NR^1$ or $NR^2$ then X is $CH_2$.

Preferred compounds of the invention include those where V, X and G are all $CH_2$, Z is OH and W is $NR^1$.

Other preferred compounds of the invention include those where V, X and G are all $CH_2$, Z is SQ and W is $NR^1$.

Preferably Y is hydrogen. Alternatively it is preferred that Y is hydroxy.

Preferably B is hydroxy. Alternatively it is preferred that B is $NH_2$.

Preferably A is CH. Alternatively it is preferred that A is N.
Preferably D is H. Alternatively it is preferred that D is $NH_2$.

It is also preferred that E is N.
Preferred compounds of the invention include:
(3R,4R)-1-[(9-deazahypoxanthin-9-yl)methyl]-3-hydroxy-4-(hydroxymethyl)pyrrolidine;
(3R,4R)-1-[(9-Deazaadenin-9-yl)methyl]-3-hydroxy-4-(hydroxylmethyl)pyrrolidine;
(3R,4R)-1-[(8-aza-9-deazahypoxanthin-9-yl)methyl]-3-hydroxy-4-(hydroxymethyl)pyrrolidine;
(3R,4R)-1-[(8-aza-9-deazaadenin-9-yl)methyl]-3-hydroxy-4-(hydroxymethyl)pyrrolidine;
(3R,4S)-1-[(9-deazaadenin-9-yl)methyl]-3-hydroxy-4-(2-phenylethyl)pyrrolidine;
(3S,4R)-1-[(9-deazahypoxanthin-9-yl)methyl]-3,4-dihydroxy-4-methylthiomethylpyrrolidine;
(3R,4S)-1-[(9-deazahypoxanthin-9-yl)methyl]-3-hydroxy-4-(methylthiomethyl)pyrrolidine;
N-(9-Deazahypoxanthin-9-yl)-1,4-dideoxy-1,4-imino-D-ribitol;

N-(9-deazahypoxanthin-9-yl)methyl-1,4-dideoxy-1,4-imino-D-ribitol;

(3R,4R)-3-hydroxy-4-hydroxymethyl-1-(hypoxanthin-9-yl)pyrrolidine;

(3R,4S)-1-[(9-deazaadenin-9-yl)methyl]-3-hydroxy-4-(methylthiomethyl)pyrrolidine;

(3R,4S)-1-[(9-deazaadenin-9-yl)methyl]-3-hydroxy-4-(benzylthiomethyl)pyrrolidine;

(3R,4S)-1-[(8-aza-9-deazaadenin-9-yl)methyl]-3-hydroxy-4-(benzylthiomethyl)pyrrolidine;

(3R,4R)-1-[(9-deazaguanin-9-yl)methyl]-3-hydroxy-4-(hydroxymethyl)pyrrolidine;

(3R,4S)-1-[(9-deazaadenin-9-yl)methyl]-3-hydroxy-4-(4-chlorophenylthiomethyl)pyrrolidine;

(3R,4R)-1-[(6-chloro-9-deazapurin-9-yl)methyl]-3-hydroxy-4-(hydroxymethyl)pyrrolidine;

(3R,4R)-1-[(6-azido-9-deazapurin-9-yl)methyl]-3-hydroxy-4-(hydroxymethyl)pyrrolidine; or (3R,4R)-1-[(9-deazaadenin-9-yl)methyl]-3-acetoxy-4-(acetoxymethyl)pyrrolidine.

In another aspect, the invention provides a pharmaceutical composition comprising a pharmaceutically effective amount of a compound of formula (I) as defined above.

In yet another aspect, the invention provides a method of treating a disease or condition in which it is desirable to inhibit purine phosphoribosyltransferase, purine nucleoside phosphorylase, 5'-methylthioadenosine phosphorylase, 5'-methylthioadenosine nucleosidase and/or nucleoside hydrolase comprising administering a pharmaceutically effective amount of a compound of formula (I) as defined above to a patient requiring treatment.

The disease or condition may Include cancer, bacterial infection, protozoal Infection or a T-cell mediated disease. The T-cell mediated disease may be psoriasis, arthritis or transplant rejection.

In still another aspect, the invention provides the use of a compound of formula (I) as defined above in the manufacture of a medicament for treating a disease or condition in which it is desirable to inhibit purine phosphoribosyltransferase, purine nucleoside phosphorylase, 5'-methylthioadenosine phosphorylase, 5'-methylthioadenosine nucleosidase and/or nucleoside hydrolase.

DETAILED DESCRIPTION

It will be appreciated that the representation of a compound of formula (I), where B and/or D is a hydroxy group, is of the enol-type tautomeric form of a corresponding amide, and this will largely exist in the amide form. The use of the enol-type tautomeric representation is simply to allow fewer structural formulae to represent the compounds of the invention.

Similarly, it will be appreciated that the representation of a compound of formula (I), where B and/or D is a thiol group, is of the thioenol-type tautomeric form of a corresponding thioamide, and this will largely exist in the thioamide form. The use of the thioenol-type tautomeric representation is simply to allow fewer structural formulae to represent the compounds of the invention.

The compounds of the invention may be prepared by any suitable method. One suitable method involves independently synthesising the sugar part and the base part and then linking the base part to a nitrogen atom in the ring of the sugar part.

For example, Scheme 1 below outlines the preparation of the 1-N-imino sugar part of a compound of the invention where the nitrogen atom of the sugar analogue is located at the same position as the C-1 anomeric carbon atom would be found in a sugar molecule. A useful starting compound in the synthesis of the 1-N-iminosugar is N-tert-butoxycarbonyl-(3R,4S)-3-hydroxy-4-[(1S)-1,2-dihydroxyethyl]pyrrolidine. This starting compound may be prepared via the method of Filichev et al. (Carbohydrate Res., 2001, 333, 115-122) with the only variation being that a t-butoxycarbonyl moiety is utilised as the nitrogen protecting group rather than the N-(9-fluorenylmethoxycarbonyl) group. Oxidative cleavage of the diol moiety followed by reduction in situ gives the N-protected 3-hydroxy-4-hydroxymethylpyrrolidine (1). Removal of the N protecting group gives (3R,4R)-3-hydroxy-4-hydroxymethylpyrrolidine (4). Racemic 3-hydroxy-4-hydroxymethyl pyrrolidine was first prepared by Jaeger et al. (J. Org. Chem., 1965, 30, 740-744) and was used in the preparation of 1'-aza carbacyclic thymidine analogues (Lee, Y. H., Kim, H. K, Youn, I. K., Chae, Y. B., Bioorg. Med. Chem. Lett. 1991, 1, 287-290.) and aza-C-pyrimidines (Sorenson, M. D., Khalifa, N. M., Pedersen, E. B., Synthesis, 1999, 1937-1943).

Two other methods for the synthesis of (3R,4R)-3-hydroxy-4-hydroxymethylpyrrolidine have also been described. One method by Bols et. al [Bols, M., Hansen, S. U., Acta Chem. Scand., 1998, 52, 1214-1222] involves enzymatic purification of the enantiomers. The other method by Ichikawa et. al [Ichikawa, Y., Makino, K., Tetrahedron Lett., 1998, 39, 8245-8248] is a multi-gram asymmetric synthesis of (3R,4R)-3-hydroxy-4-hydroxymethylpyrrolidine via fumaric acid monoethyl ester. Ichikawa et. al evaluated the inhibitory activity of (3R,4R)-3-hydroxy-4-hydroxymethylpyrrolidine against human PNP and obtained an $IC_{50}$ of 160 µM.

Benzylation of the hydroxyl groups of compound (1) before removal of the N protecting group may be desirable to give (3R,4R)-3-benzyloxy-4-benzyloxymethylpyrrolidine hydrochloride (3) as a useful compound ready for linking to a suitable base analogue.

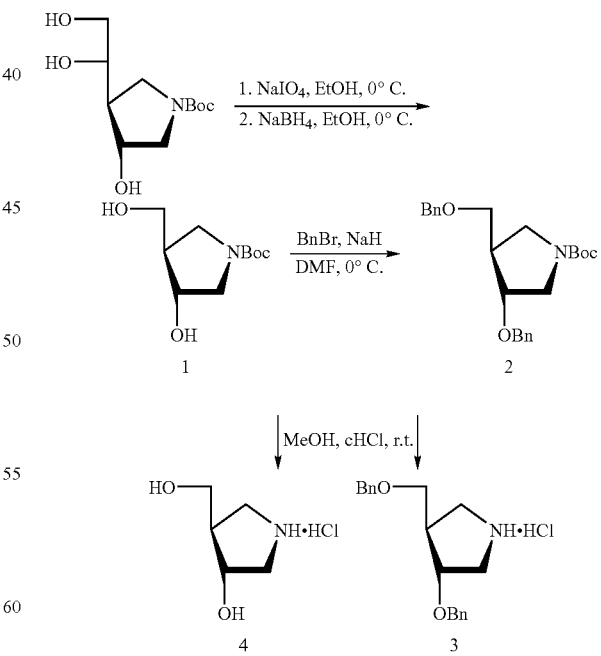

Scheme 1

The linking of the sugar part may be achieved by reductive amination of an appropriate aldehyde. Examples of suitable aldehydes, prepared from their corresponding bromo precursors, are shown in Scheme 2.

Scheme 2

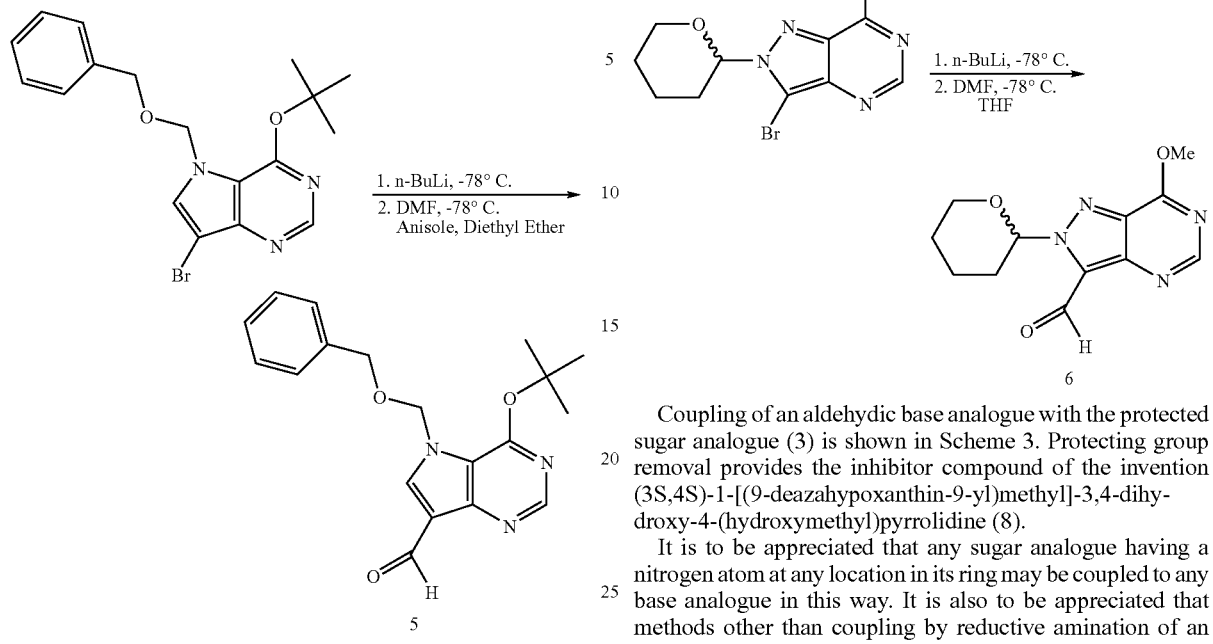

Coupling of an aldehydic base analogue with the protected sugar analogue (3) is shown in Scheme 3. Protecting group removal provides the inhibitor compound of the invention (3S,4S)-1-[(9-deazahypoxanthin-9-yl)methyl]-3,4-dihydroxy-4-(hydroxymethyl)pyrrolidine (8).

It is to be appreciated that any sugar analogue having a nitrogen atom at any location in its ring may be coupled to any base analogue in this way. It is also to be appreciated that methods other than coupling by reductive amination of an aldehyde may be used.

Scheme 3

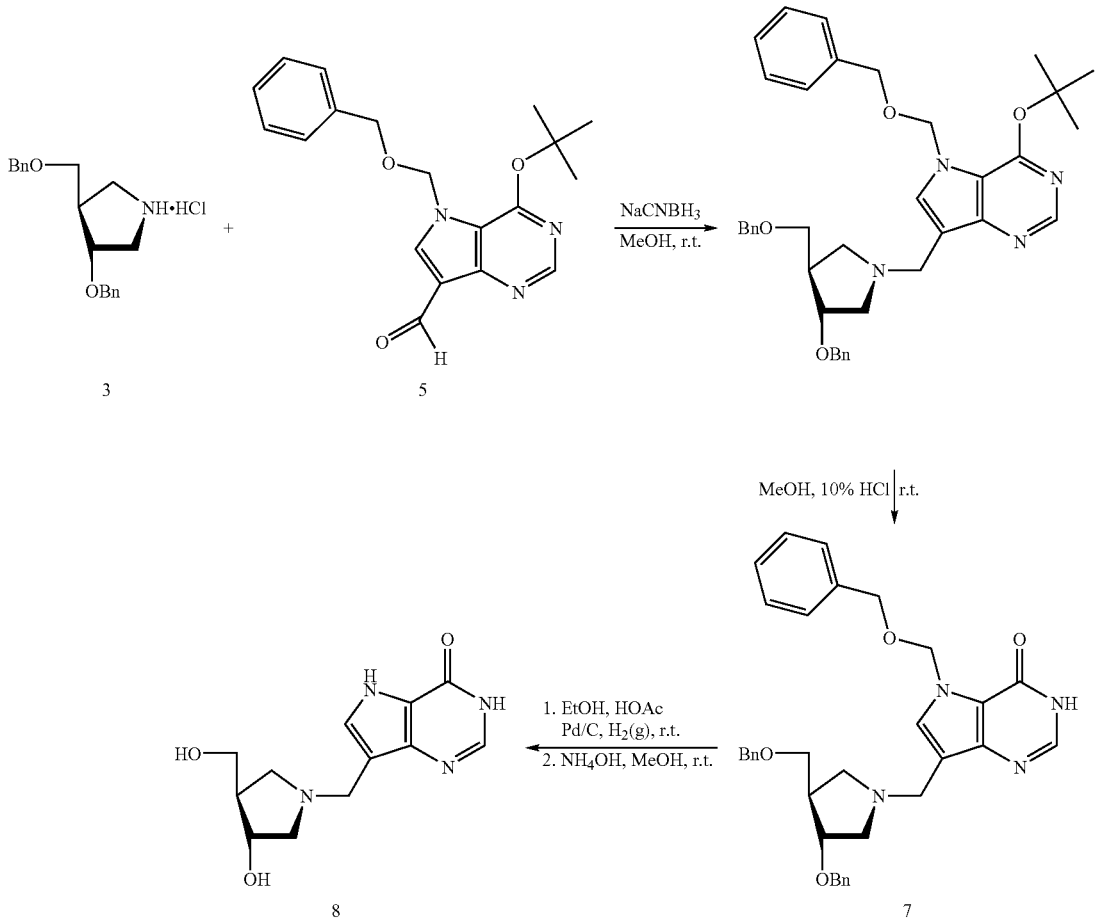

As can be seen from Scheme 4 below, the intermediate (7) may be manipulated to afford (10).

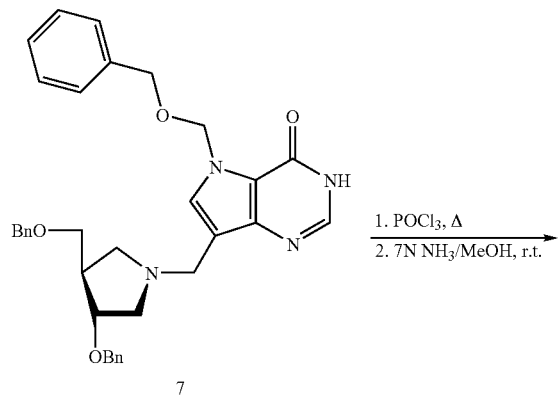

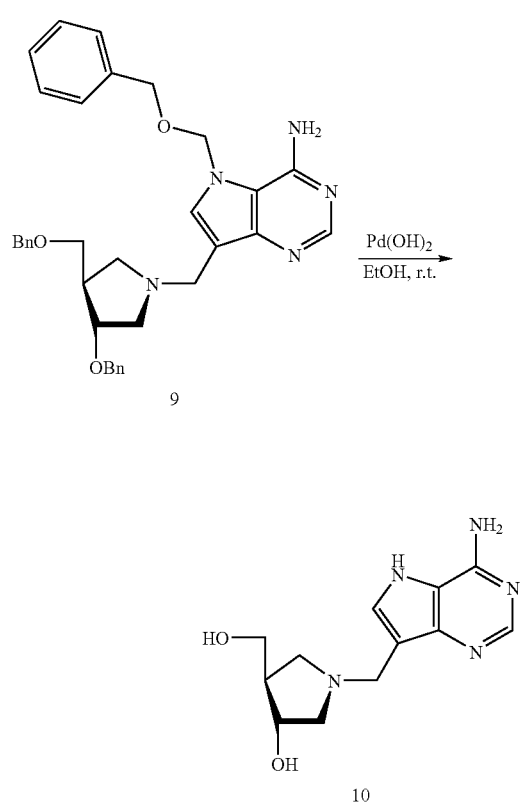

Other examples of the coupling of base analogues to the sugar analogue (4) are shown in Scheme 5. This method can be used to prepare the compounds (3R,4S)-1-[(8-aza-9-deazahypoxanthin-9-yl)methyl]-3-hydroxy-4-(hydroxymethyl)pyrrolidine; (12) and (3R,4S)-1-[(8-aza-9-deazaadenin-9-yl)methyl]-3-hydroxy-4-(hydroxymethyl)pyrrolidine (13).

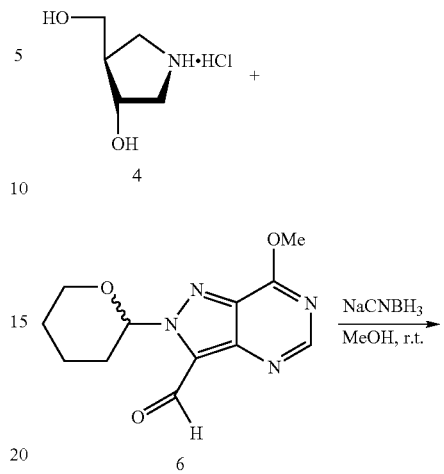

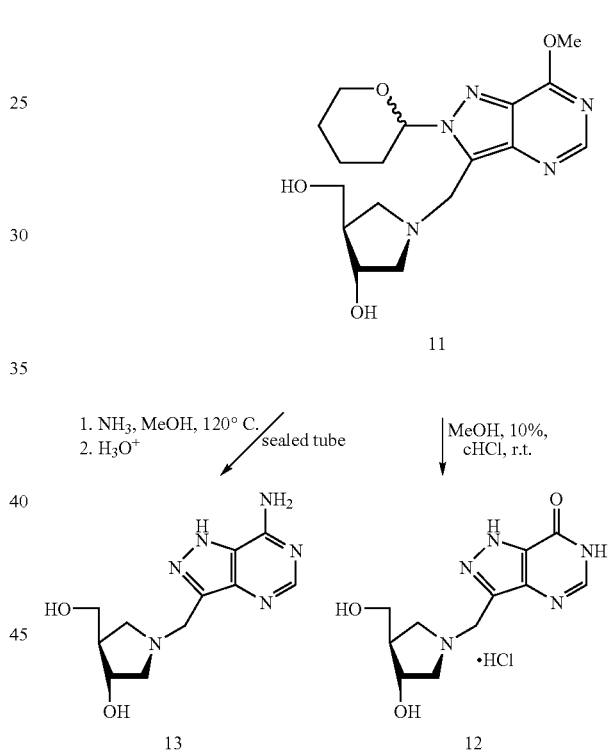

An intermediate sugar analogue containing two nitrogen atoms in its ring has been prepared. (3R,4S)-4-Hydroxy-3-hydroxymethylpyrazolidine (21) may be prepared according to the route outlined in Scheme 6. The ketone (14) is prepared from D-xylose using well known chemistry (Lin, T-S., Zhu, J-L., Dutschman, G. E., Cheng, Y-C., Prusoff, W. H., *J. Med. Chem.* 1993, 36, 353-362). Amination followed by reduction of the imine and acetylation of the resulting secondary amine gives compound (17). The key step of acid hydrolysis with concomitant recyclisation gives the imino cycle (18). Hydrogenation followed by cleavage of the diol moiety and removal of the acetate provides the desired pyrazolidine (21).

The pyrazolidine (21), or the precursor N-acetate (20), may be coupled with a variety of base analogues to give potential inhibitors of the formula (I) of this invention.

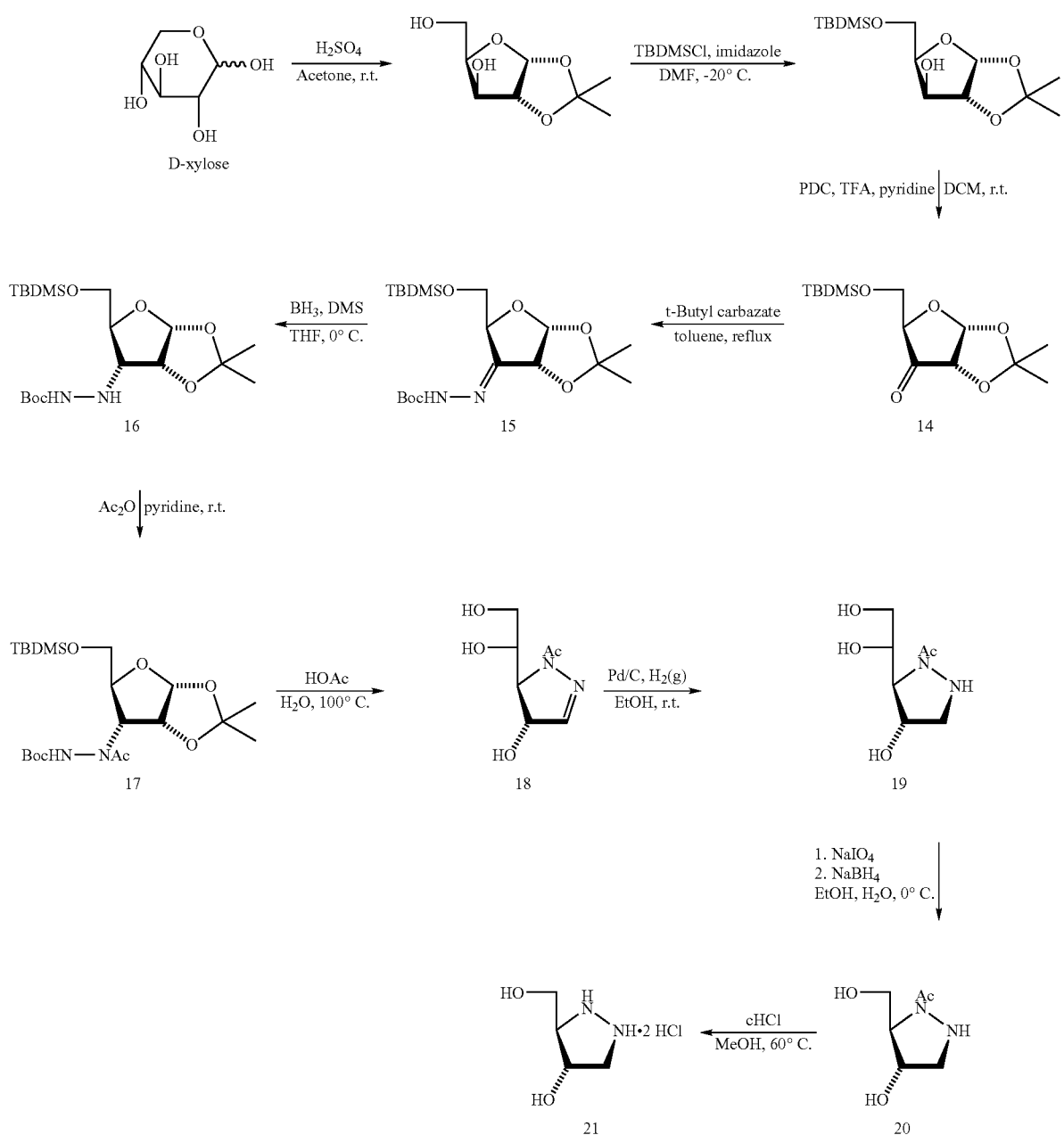

An alternative method for coupling the base analogue to the sugar analogue is shown in Scheme 7. The aldehyde N-tert-butoxycarbonyl-(3R,4S)-3-hydroxy-4-formylpyrrolidine (22) is employed in a Wittig-type reaction to provide the 5'C—C linked intermediate N-tert-butoxycarbonyl-(3R,4R)-3-hydroxy-4-(2-phenylethenyl)pyrrolidine (23). Subsequent hydrogenation and Boc-cleavage provides the hydrochloride salt (25) which can be used in a Mannich-type reaction to provide (3R,4R)-1-[(6-chloro-9-deazapurin-9-yl)methyl]-3-hydroxy-4-(2-phenylethyl)pyrrolidine (26). Treatment with 7 N ammonia in methanol at 130° C. in a sealed tube followed by the transformation to the hydrochloride salt with 3N aqueous HCl gives (3R,4S)-1-[(9-deazaadenin-9-yl)methyl]-3-hydroxy-4-(2-phenylethyl)pyrrolidine hydrochloride (27).

It will be appreciated that the route exemplified in Scheme 7 can be applied to the coupling of a variety of analogues of 25 varying in the C-4 substituent with a variety of 9-deazapurine analogues.

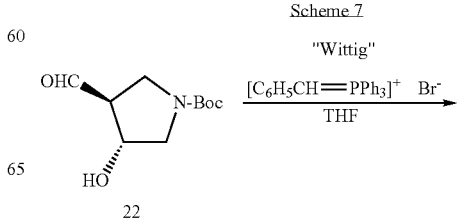

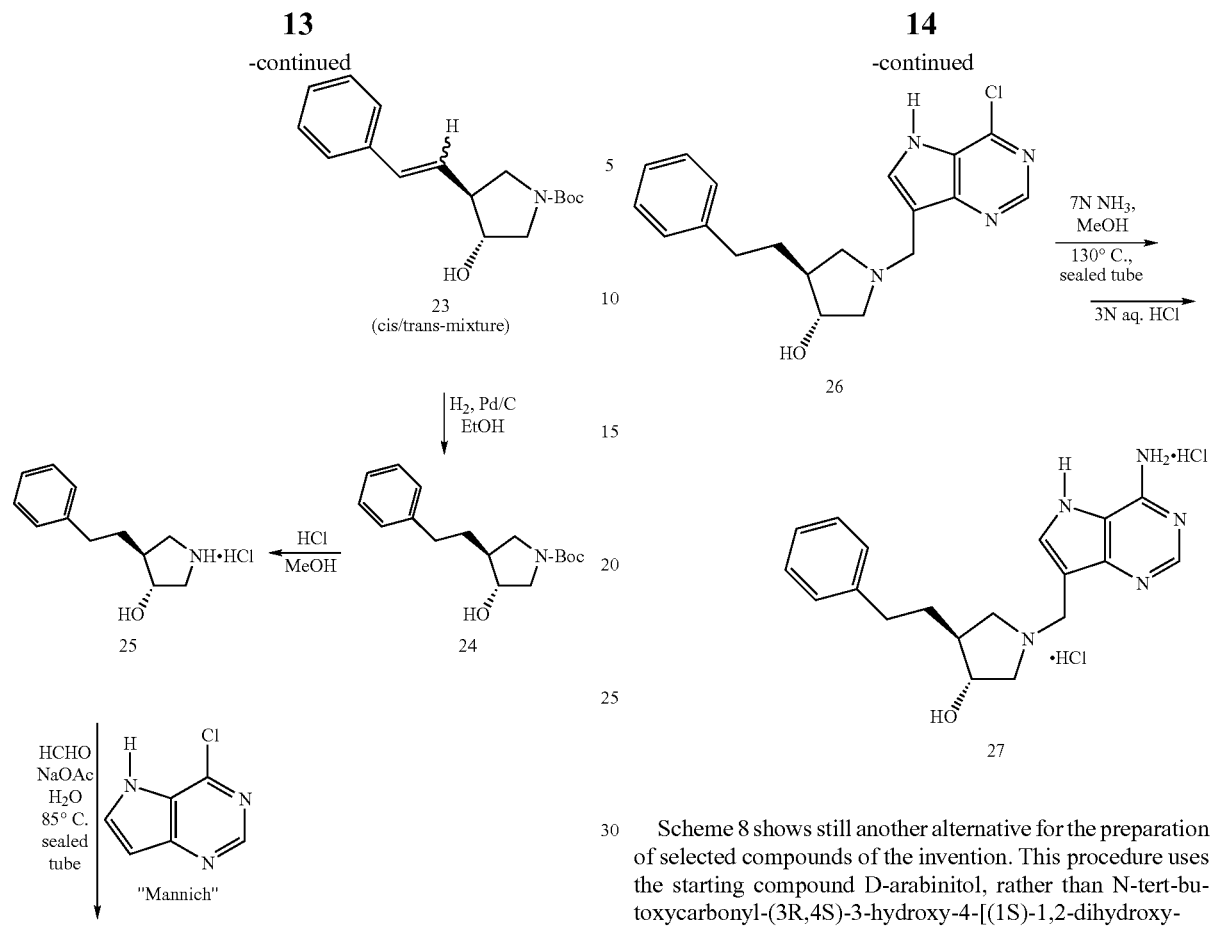
Scheme 8 shows still another alternative for the preparation of selected compounds of the invention. This procedure uses the starting compound D-arabinitol, rather than N-tert-butoxycarbonyl-(3R,4S)-3-hydroxy-4-[(1S)-1,2-dihydroxyethyl]pyrrolidine.
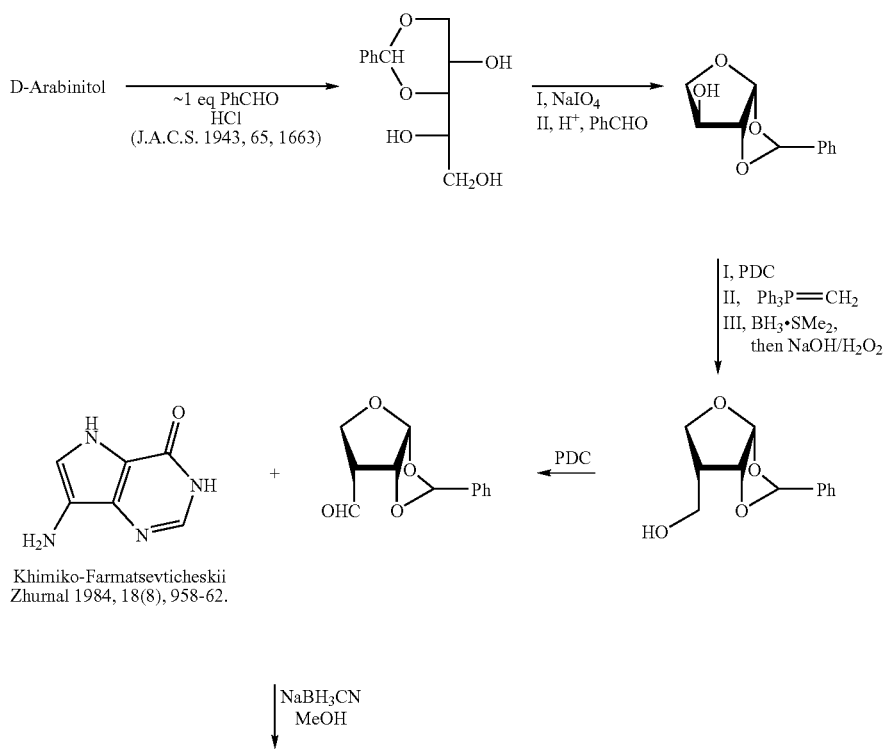

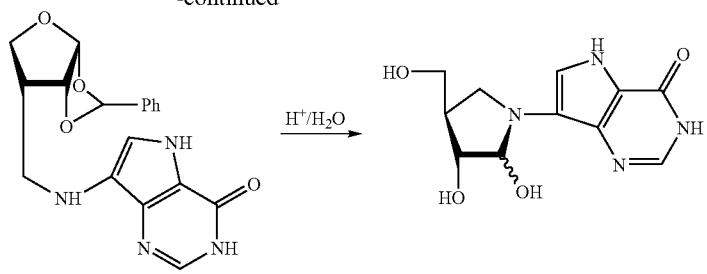

The compounds of the invention are potent inhibitors of PNP, MTAP and/or MTAN. Table 1 shows inhibition constants for selected compounds of the invention against human PNP. Table 2 shows inhibition constants for selected compounds against *E. coli* MTAN. Table 3 shows inhibition constants for selected compounds against human MTAP. Table 4 shows inhibition constants for selected compounds against *Mycobacterium tuberculosis* PNP. Table 5 shows inhibition constants for selected compounds against *Plasmodium falciparum* PNP.

TABLE 1

| Inhibition Constants against Human PNP | | | |
|---|---|---|---|
| Compound No. | Structure | Ki | Ki* |
| 61 | | 163 ± 25 pM | 6.8 ± 1.2 pM |
| 8 | | 1100 ± 120 pM | 16.0 ± 1.4 pM |
| 12 | | 2000 ± 50 pM | No slow onset |
| 33 | | 433 ± 13 nM | No slow onset |

TABLE 1-continued
Inhibition Constants against Human PNP
| Compound No. | Structure | Ki | Ki* |
|---|---|---|---|
| 37 | 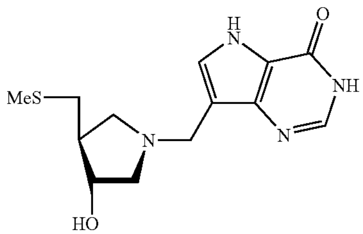 | 19.6 ± 3.5 pM | No slow onset |
| 31 | 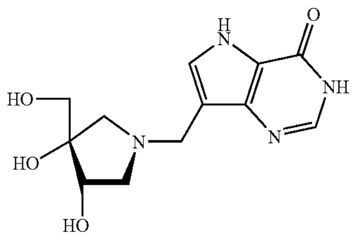 | 14 ± 3 nM | No slow onset |
| 41 | 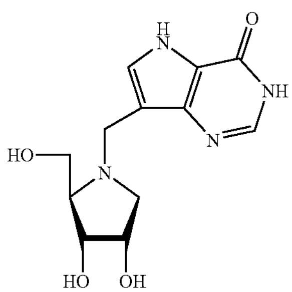 | 2.8 nM | No slow onset |
| 40 | 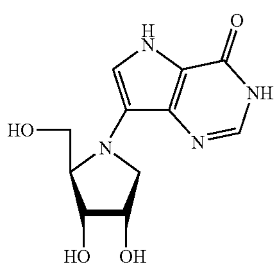 | 12.7 μM | No slow onset |
TABLE 2
Inhibition Constants against *E. coli* MTAN
| Compound No. | Structure | Ki | Ki* |
|---|---|---|---|
| 52 | 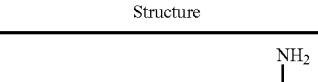 | 17 ± 2 pM | 160 ± 14 fM |

TABLE 2-continued
Inhibition Constants against *E. coli* MTAN
| Compound No. | Structure | Ki | Ki* |
|---|---|---|---|
| 57 | 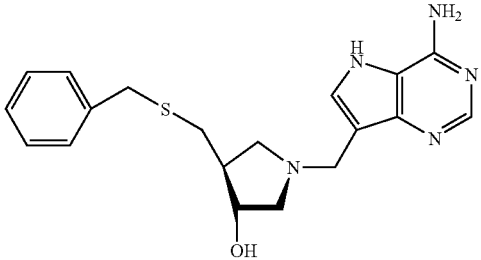 | 9.0 ± 1 pM | 42 ± 5 fM |
| 58 | 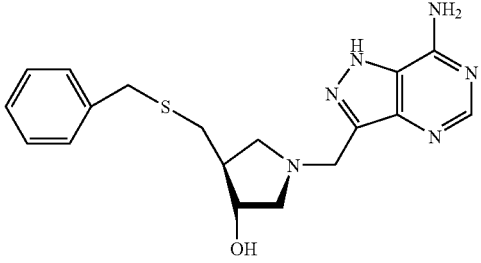 | | 190 fM |
| 62 | 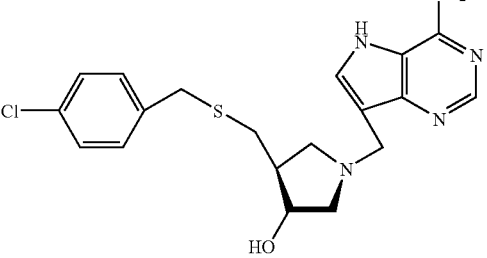 | 4.0 ± 0.4 pM | 91 ± 2.0 fM |
| 27 | 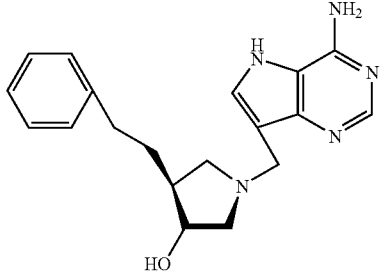 | 47.0 ± 8.0 nM | 1.0 ± 0.3 nM |

TABLE 3

Inhibition Constants against Human MTAP

| Compound No. | Structure | Ki | Ki* |
|---|---|---|---|
| 52 | (structure) | 870 ± 110 pM | 22 ± 3 pM |
| 62 | (structure) | 46.0 ± 8.0 pM | <3 pM |
| 27 | (structure) | No inhibition at 10 micomolar | |
| 57 | (structure) | 280 ± 50 pM | 3.0 ± 0.3 pM |
| 58 | (structure) | 51 nM | No slow onset |

TABLE 4

Inhibition Constants against *Mycobacterium tuberculosis* PNP

| Compound No. | Structure | Ki | Ki* |
|---|---|---|---|
| 8 | (pyrrolo[3,2-d]pyrimidin-4(5H)-one with 3,4-dihydroxypyrrolidinylmethyl substituent) | 1.3 ± 0.1 nM | 42.2 ± 2 pM |
| 61 | (2-amino-pyrrolo[3,2-d]pyrimidin-4(5H)-one with 3,4-dihydroxypyrrolidinylmethyl substituent) | 540 ± 40 pM | 24 ± 1 pM |
| 12 | (pyrazolo[3,4-d]pyrimidin-4(5H)-one with 3,4-dihydroxypyrrolidinylmethyl substituent) | 2.1 ± 0.2 nM | No slow onset |
| 41 | (pyrrolo[3,2-d]pyrimidin-4(5H)-one with 3,4-dihydroxypyrrolidinylmethyl substituent, alternate stereochemistry) | 7 ± 0.2 nM | No slow onset |

TABLE 5

Inhibition Constants against *Plasmodium falciparum* PNP

| Compound No. | Structure | Ki | Ki* |
|---|---|---|---|
| 37 | (pyrrolo[3,2-d]pyrimidin-4(5H)-one with 3-hydroxy-4-(methylthio)pyrrolidinylmethyl substituent) | 20.4 ± 1.8 nM | No slow onset |

TABLE 5-continued

Inhibition Constants against *Plasmodium falciparum* PNP

| Compound No. | Structure | Ki | Ki* |
|---|---|---|---|
| 33 | (structure with MeS, HO, HO substituents on pyrrolidine linked to deazahypoxanthine) | 45 ± 3 μM | No slow onset |
| 8 | (structure with HO, HO substituents on pyrrolidine linked to deazahypoxanthine) | 500 pM | No slow onset |
| 31 | (structure with HO, HO, HO substituents on pyrrolidine linked to deazahypoxanthine) | 4.3 μM | No slow onset |

$K_i$ as shown in Tables 1, 2, 3 4 and 5 is the initial inhibition constant formed by the enzyme-inhibitor complex, and $K_i^*$ is the equilibrium dissociation constant for inhibition that is observed following a period of slow-onset, tight binding inhibition. Ki* is the biologically effective constant.

Further Aspects

The compounds of the invention are useful in both free base form and in the form of salts. The term "pharmaceutically acceptable salts" is intended to apply to non-toxic salts derived from inorganic or organic acids, including, for example, the following acids: hydrochloric, sulphuric, phosphoric, acetic, lactic, fumaric, succinic, tartaric, gluconic, citric, methanesulfonic and p-toluenesulfonic acids.

The active compounds may be administered to a patient by a variety of routes, including oral administration, injection, or topical administration. The amount of compound to be administered will vary widely according to the nature of the patient and the nature and extent of the disorder to be treated. Typically the dosage for an adult human will be in the range less than 1 to 1000 milligrams, preferably 0.1 to 100 milligrams.

For oral administration the compounds can be formulated into solid or liquid preparations, for example tablets, capsules, powders, solutions, suspensions and dispersions. Such preparations are well known in the art as are other oral dosage regimes not listed here. In the tablet form the compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid and the lubricant may be magnesium stearate. Other components such as colourings or flavourings may be added.

Liquid forms include carriers such as water and ethanol, with or without other agents such as a pharmaceutically acceptable surfactant or suspending agent.

The compounds may also be administered by injection in a physiologically acceptable diluent such as water or saline. The diluent may comprise one or more other ingredients such as ethanol, propylene glycol, an oil or a pharmaceutically acceptable surfactant.

The compounds may be present as Ingredients in creams, for topical administration to skin or mucous membranes. Preferably the creams include a pharmaceutically acceptable solvent to assist passage through the skin or mucous membranes. Suitable creams are well known to those skilled in the art.

The compounds may further be administered by means of sustained release systems. For example, they may be incorporated into a slowly dissolving tablet or capsule.

EXAMPLES

Figure 1:
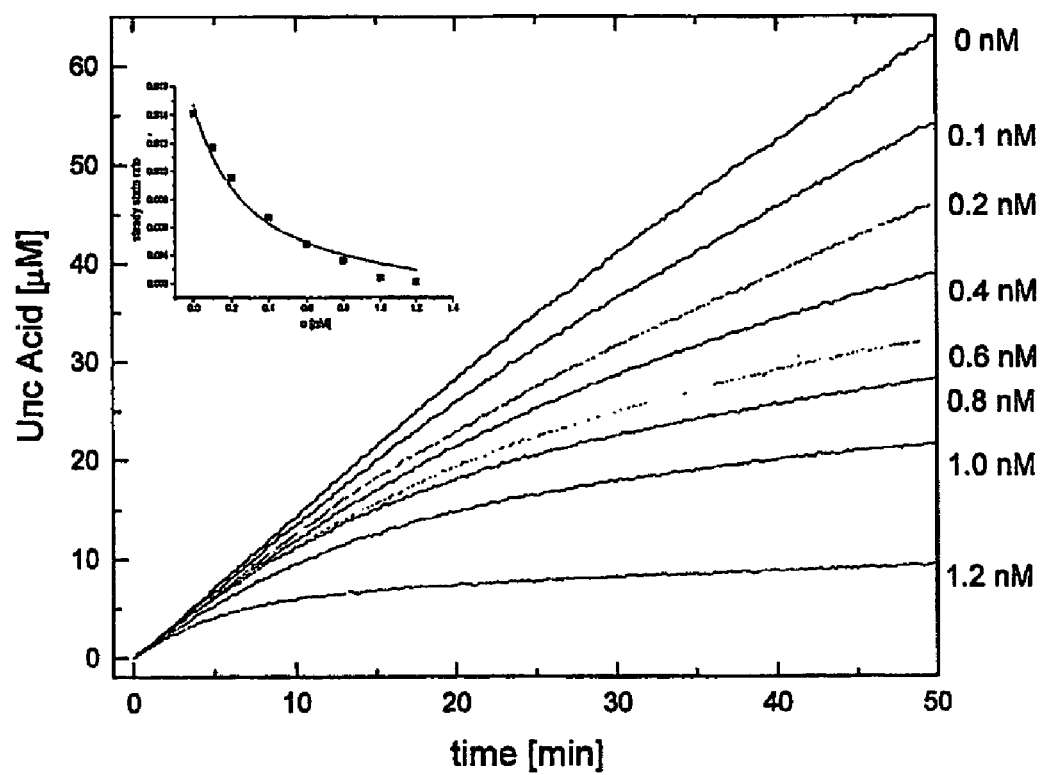
FIG. 1 shows the kinetic curves for human PNP inhibited by compound (8).

The following examples further illustrate the invention. It is to be appreciated that the invention is not limited to the examples.

Scheme 1

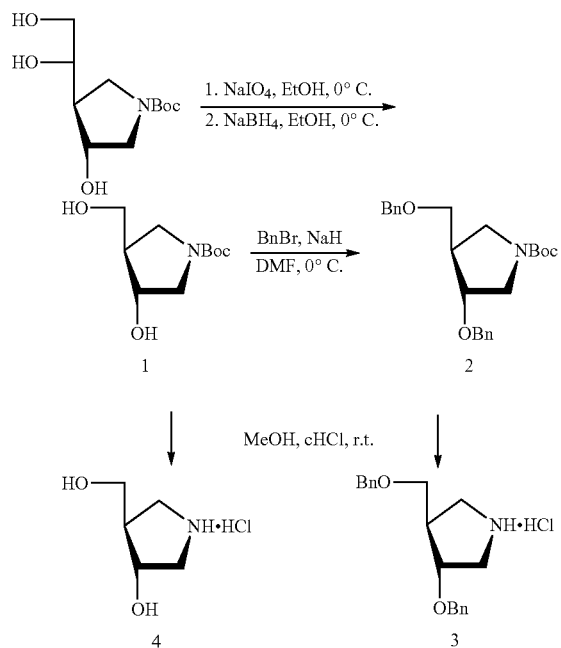

Example 1

N-tert-Butoxycarbonyl-(3R,4R)-3-hydroxy-4-(hydroxymethyl)pyrrolidine (1). N-tert-Butoxycarbonyl-(3R,4S)-3-hydroxy-4-[(1S)-1,2-dihydroxyethyl]pyrrolidine (3.4 g, 13.7 mmol) in ethanol (50 mL) was added dropwise to a stirred solution of sodium periodate (3.4 g, 16 mmol) in water (25 mL) while maintaining the reaction temperature at 0° C. The reaction was left an additional 20 min after which time sodium borohydride (2.0 g, excess) was added portionwise while again ensuring the reaction temperature was maintained at 0° C. On complete addition the solid was filtered, washed with ethanol (50 mL) and concentrated in vacuo to afford a syrup. Chromatography afforded 1 (2.74 g, 92%) as a syrup.

Example 2

N-tert-Butoxycarbonyl-(3R,4R)-3-benzyloxy-4-(benzyloxymethyl)pyrrolidine (2). Sodium hydride (140 mg, 60% oil dispersion, 3.7 mmol) was added portionwise to a stirred solution of benzyl bromide (300 μL, 2.8 mmol) and 1 (200 mg, 0.92 mmol) in DMF (10 mL) at 0° C. On complete addition the resulting suspension was allowed to warm to r.t., diluted with toluene (100 mL), washed with water (50 mL), brine (50 mL), dried (MgSO$_4$), and concentrated in vacuo to afford a syrup. Chromatography afforded 2 (350 mg, 96%) as an oil which was used in the next step without purification.

Example 3

(3R,4R)-3-Benzyloxy-4-(benzyloxymethyl)pyrrolidine hydrochloride (3). Hydrochloric acid (2 mL, 1M) was added to a solution of 2 (500 mg, 1.3 mmol) in methanol (2 mL) and the resulting mixture stirred for 1 h at 40° C. On completion the reaction was concentrated in vacuo to afford 3 as the hydrochloride salt (330 mg, 90%). $^1$H NMR δ 7.35-7.21 (m, 10H), 4.48 (m, 4H), 4.08 (d, J=2.9 Hz, 1H), 3.53 (m, 1H), 3.44 (m, 3H), 3.24 (m, 1H), 2.65 (m, 1H). $^{13}$C NMR δ 138.0, 137.6, 128.9, 128.8, 128.3, 128.2, 79.3, 73.7, 71.9, 68.7, 49.6, 46.4, 44.8.

Example 4

(3R,4R)-3-Hydroxy-4-(hydroxymethyl)pyrrolidine (4). Hydrochloric acid (5 mL, 12M) was added dropwise to a stirred solution of 1 (2.3 g, 10.6 mmol) in methanol (5 mL) at room temperature. After 1 h the reaction was concentrated in vacuo to afford 4 (1.63 g, 100%) as an oil. $^{13}$C NMR δ 71.9, 60.9, 52.1, 47.9, 46.6.

Scheme 2

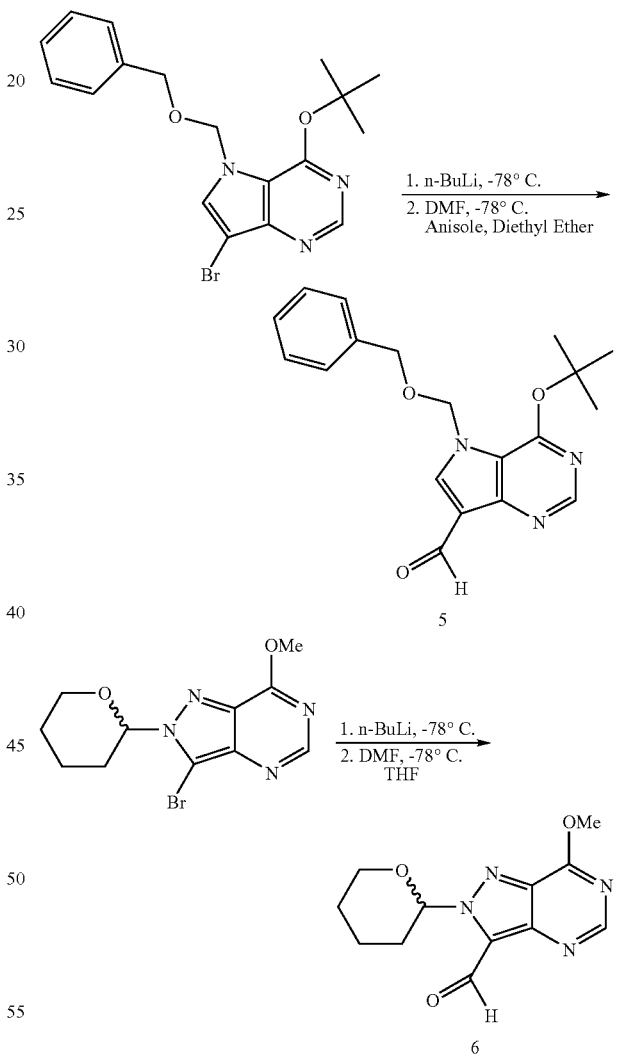

Example 5

7-N-Benzyloxymethyl-6-tert-butoxy-9-deazapurine-9-carbaldehyde (5). 5-Benzyloxymethyl-7-bromo-4-tert-butoxypyrrolo[3,2-d]pyrimidine (400 mg, 1.02 mmol) was dissolved in diethyl ether (10 mL) and anisole (5 mL) and cooled to −78° C. n-Butyl lithium (600 μL, 2.5 M) was then added dropwise at such a rate as to maintain the reaction temperature below −70° C. and the resulting solution left for 30 min at −78° C. Dimethylformamide (100 μL) was then added and the reaction left stirring for an additional 30 min and then quenched with water and allowed to warm to r.t. The reaction was then diluted with ethyl acetate (100 mL), washed with water (30 mL), brine (30 mL), dried (MgSO₄) and concentrated in vacuo to afford a syrup. Purification by chromatography afforded 5 (270 mg, 78%). ¹H NMR δ 10.29 (s, 1H), 8.62 (s, 1H), 7.98 (s, 1H), 7.34-7.22 (m, 5H), 5.79 (s, 2H), 4.53 (s, 2H), 1.71 (s, 9H). ¹³C NMR δ 184.8, 156.63, 152.6, 150.0, 136.7, 136.6, 128.9, 128.5, 127.8, 118.4, 84.4, 78.3, 71.0, 29.0.

Example 6

8-Aza-9-deaza-6-methoxy-7-N-(tetrahydropyran-2-yl)-purine-9-carbaldehyde (6). nBuLi (0.7 mL, 2.4 M) was added dropwise to a stirred solution of 8-aza-9-bromo-9-deaza-6-methoxy-7-N-(tetrahydropyran-2-yl)-purine (530 mg, 1.7 mmol) in THF (20 mL) at −78° C. under an inert atmosphere. The reaction was stirred for an additional 30 min at −78° C. and then DMF (1.0 mL) was added and the reaction allowed to warm to room temperature. The reaction was quenched with water (50 mL) extracted with toluene (2×100 mL), the organic layers were combined washed with brine, dried (MgSO₄), filtered and concentrated in vacuo to afford a solid residue. Chromatography afforded 6 as a solid. ¹H NMR δ 10.43 (s, 1H), 8.71 (s, 1H), 6.55 (dd, J=10.0, 2.7 Hz, 1H), 4.25 (s, 3H), 4.13 (m, 1H), 3.83 (dt, J=10.8, 2.8 Hz), 2.53-1.65 (m, 7H). ¹³C NMR δ 177.0, 161.5, 154.5, 143.9, 130.2, 128.9, 87.0, 67.4, 53.5, 28.7, 23.7, 21.2.

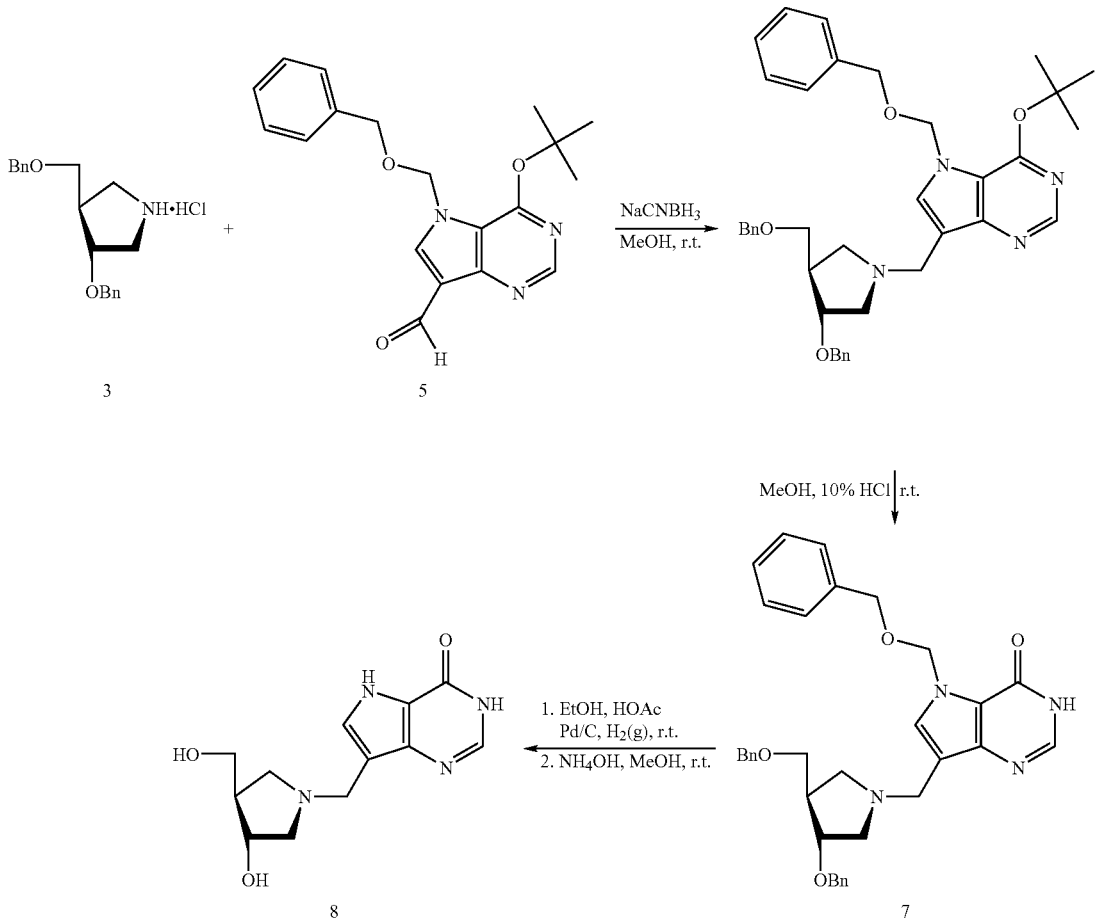

Scheme 3

Example 7

7-[(3R,4R)-(3-Benzyloxy-4-benzyloxymethylpyrrolidin-1-yl)methyl]-5-benzyloxymethyl-3H-pyrrolo[3,2-d]pyrimidin 4-one(3S,4S)-1-[(9-deaza-7-benzyloxymethyl-hypoxanthin-9-yl)methyl]-3-benzyloxy-4-(benzyloxymethyl) pyrrolidine (7). Sodium cyanoborohydride (100 mg, 1.59 mmol) was added to a stirred solution of 5 (220 mg, 0.64 mmol) and 3.HCl (190 mg, 0.57 mmol) in methanol (5 mL) and stirred overnight at r.t. The reaction was then concentrated in vacuo and redissolved in methanol (2 mL) and cHCl (2 mL), stirred for 1 h and then concentrated in vacuo to afford a solid residue. Chromatography of the resulting residue afforded 7 (202 mg, 63%) as a solid. ¹H NMR δ 7.87 (1H, s), 7.32 (1H, s), 7.31-7.23 (m, 5H), 5.89 (s, 2H), 4.56 (s, 2H), 4.50 (s, 2H), 4.48 (s, 2H), 4.47 (s, 2H), 3.87 (m, 2H), 3.81 (q, J=13.4 Hz, 2H), 3.43 (d, J=7.1 Hz, 2H), 3.01 (t, J=8.1 Hz, 1H), 2.79 (d, J=4.7 Hz, 1H), 2.55 (m, 1H), 2.36 (m, 1H). ¹³C NMR δ 156.2, 145.8, 141.8, 138.9, 138.8, 137.6, 131.4, 128.8, 128.7, 128.3, 128.2, 128.1, 128.0, 128.8, 117.9, 115.7, 81.3, 77.1, 73.5, 72.1, 71.4, 70.8, 60.0, 56.4, 48.6, 45.9.

Example 8

(3R,4R)-1-[(9-deazahypoxanthin-9-yl)methyl]-3-hydroxy-4-(hydroxymethyl)pyrrolidine (8). Compound 7 (120 mg, 0.21 mmol) and Pearlman's catalyst (120 mg) were suspended in ethanol (3 mL) and acetic acid (1 mL) and vigorously stirred under an atmosphere of hydrogen gas for 24 h at r.t. The reaction was then filtered through celite and concentrated in vacuo to afford a solid. Chromatography and ion exchange of the solid afforded 8 (38 mg, 68%) as a white solid with m.p. 248-250° C. $^1$H NMR δ 7.81 (1H, s), 7.34 (1H, s), 3.97 (1H, brs), 3.65 (2H, s), 3.53 (1H, m), 3.44 (1H, m), 2.93 (1H, t, J=9.0 Hz), 2.77 (1H, m), 2.60 (1H, m), 2.33 (1H, t, J=7.1 Hz), 2.12 (1H, brs). $^{13}$C NMR δ 155.8, 144.1, 142.8, 130.0, 117.3, 111.1, 72.9, 62.7, 60.2, 54.8, 48.9, 47.3. HRMS (MH+) calc. for $C_{12}H_{16}N_4O_3$: 265.1301. Found 265.1302. Anal. Calc. for $C_{12}H_{11}N_4O_3 \cdot \frac{1}{2}H_2O$ C, 52.7; H, 6.2; N, 20.5. Found C, 53.0; H, 5.9; N, 20.4.

Scheme 4

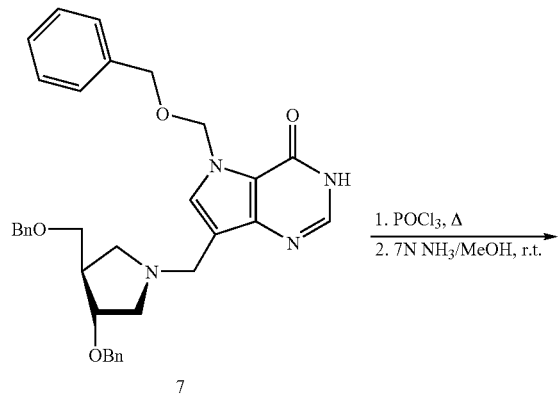

Example 9.1

(3R,4R)-1-[(9-deaza-7-benzyloxymethyl-adenin-9-yl)methyl]-3-benzyloxy-4-(benzyloxymethyl)pyrrolidine (9). Compound 7 (1.2 g, 2.12 mmol) was added to phosphoryl chloride (20 mL) and the resulting suspension heated to reflux. After 1 h the reaction was concentrated in vacuo, diluted with chloroform, washed with saturated NaHCO$_3$, brine, dried (MgSO$_4$), and concentrated in vacuo. The resulting residue was redissolved in 7N NH$_3$ in methanol and the resulting solution heated to 120° C. in a sealed tube overnight. The reaction was concentrated in vacuo and purified by chromatography to afford 9 (0.83 g, 69%). $^1$H NMR δ 8.38 (s, 1H), 7.76 (brs, 1H), 7.32-7.25 (m, 15H), 6.01 (brs, 2H), 5.51 (d, J=2.3 Hz, 2H), 4.55 (s, 2H), 4.51 (s, 2H), 4.48 (s, 2H), 4.25 (d, J=2.9 Hz, 2H), 4.05 (m, 1H), 3.50 (d, J=6.5 Hz, 2H), 3.42 (m, 1H), 3.31 (m, 1H), 3.20 (m, 1H), 3.01 (m, 1H), 2.71 (m, 1H). $^{13}$C NMR δ 152.3, 151.5, 150.1, 138.3, 138.0, 135.7, 134.6, 129.2, 129.0, 128.8, 128.2, 128.1, 115.18, 107.94, 79.7, 77.6, 73.6, 71.9, 70.7, 69.8, 58.6, 58.1, 55.22, 54.9, 48.8, 45.3.

Example 9.2

(3R,4R)-1-[(9-Deazaadenin-9-yl)methyl]-3-hydroxy-4-(hydroxylmethyl)pyrrolidine (10). Compound 9 (100 mg, 0.18 mmol) and Pd/C (50 mg, 10% bw) were suspended in ethanol (4 mL) and vigorously stirred under an atmosphere of hydrogen for 24 h at room temp. The reaction was then filtered through celite and concentrated in vacuo to afford a syrup. Chromatography on silica gel afforded 10 as a solid. $^1$H NMR (D$_2$O) δ 7.83 (s, 1H), 7.13 (s, 1H), 3.88 (q, J=4.4 Hz, 1H), 3.56-3.32 (4H, m), 2.78 (t, J=9.0 Hz, 1H), 2.62 (dd, J=10.7, 6.4 Hz, 1H), 2.47 (dd, J=10.7, 4.2 Hz, 1H), 2.16 (dd, J=9.8, 7.0 Hz, 1H), 2.03 (1H, m). $^{13}$C NMR (D$_2$O) δ 150.1, 149.6, 145.1, 129.6, 113.3, 109.8, 72.9, 62.8, 60.3, 54.8, 49.0, 47.3. HRMS (MH$^+$) calc for $C_{12}H_{18}N_5O_2$: 264.1461. Found 264.1457.

Scheme 5

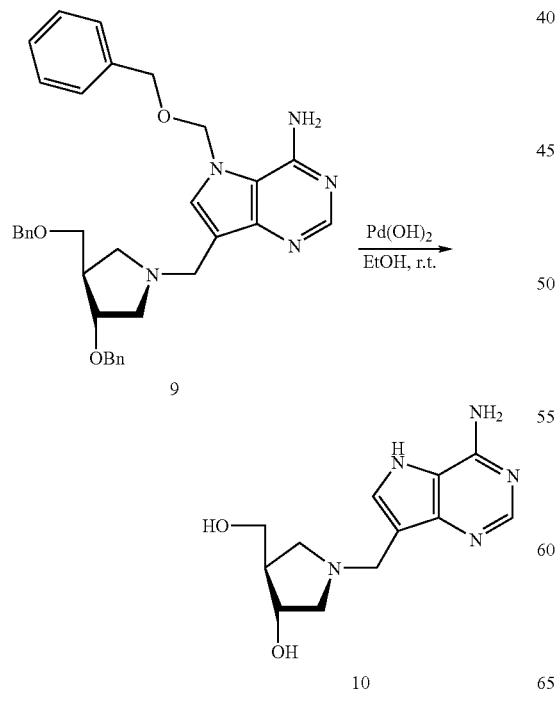

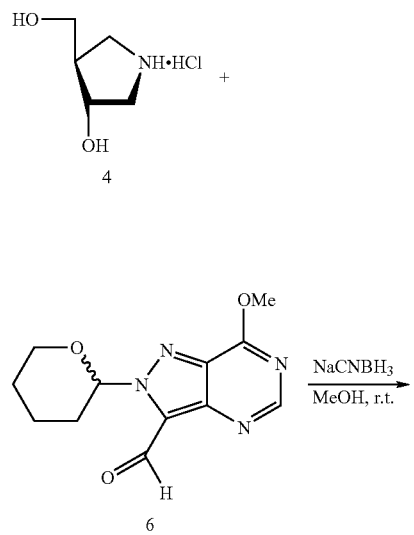

-continued

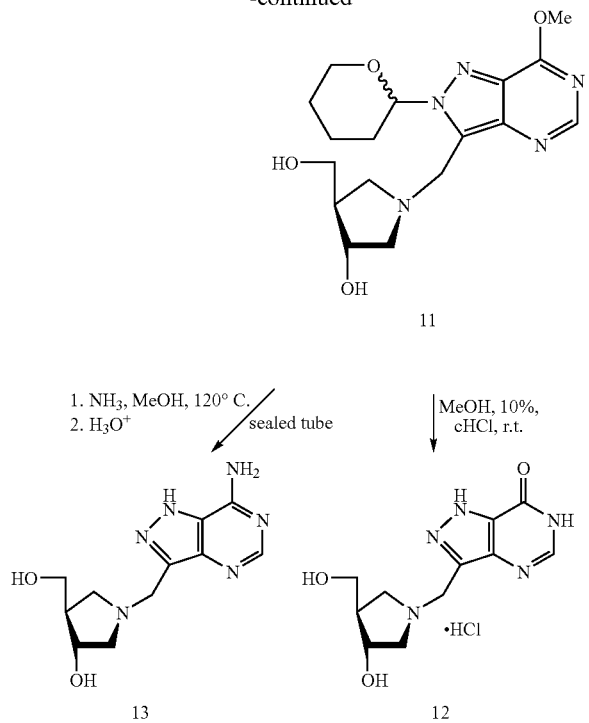

Example 10

(3R,4R)-1-[(8-Aza-9-deaza-6-methoxy-8-(tetrahydropyran-2-yl)-purin-9-yl)methyl]-3-hydroxy-4-(hydroxymethyl)pyrrolidine (11). Sodium cyanoborohydride (100 mg, 1.59 mmol) was added to a stirred solution of 6 (340 mg, 1.3 mmol) and 4.HCl (190 mg, 0.57 mmol) in methanol (5 mL) and stirred overnight at r.t. Chromatography of the resulting residue afforded 11 (150 mg, 35%) as a solid. $^1$H NMR δ 8.39 (s, 1H), 5.90 (d, J=9.1 Hz, 1H), 4.17-3.94 (m, 4H), 4.12 (s, 3H), 3.67-3.52 (m, 2H), 2.94-2.79 (m, 2H), 2.66-2.52 (m, 2H), 2.35-2.09 (m, 2H), 1.70-1.56 (m, 2H). $^{13}$C NMR δ 162.6, 152.2, (140.1, 140.0), 133.5, 131.6, (87.0, 86.9), 74.3, (68.3, 68.2), (64.3, 64.2), 62.6, (56.2, 56.1), 54.5, (50.6, 50.7), (47.7, 47.6), 29.7, 25.2, 21.8.

Example 11

(3R,4R)-1-[(8-Aza-9-deazahypoxanthin-9-yl)methyl]-3-hydroxy (hydroxymethyl)pyrrolidine (12). Concentrated hydrochloric acid (1 mL, 12M) was added to a solution of 11 (50 mg, 0.14 mmol) in methanol and stirred overnight and then concentrated in vacuo to afford a solid residue which was triturated with methanol and filtered to afford 12 (38 mg, 92%) as a solid. $^1$H NMR δ 8.13 (s, 1H), 4.35 (d, J=2.7 Hz, 1H), 3.86 (m, 1H), 3.66-3.43 (m, 2H), 3.55 (d, J=5.7 Hz, 2H), 3.10 (m, 1H), 2.44 (brs, 1H). $^{13}$C NMR δ 154.7, 145.4, 137.1, 134.7, 128.6, 71.4, 60.6, 60.6, 55.0, 48.0, 47.9.

Example 12

(3R,4R)-1-[(8-Aza-9-deazaadenin-9-yl)methyl]-3-hydroxy-4-(hydroxymethyl)pyrrolidine (13). A solution of 11 (100 mg) in 7 N NH$_3$ in methanol (4 mL) was heated in a sealed tube at 120° C. overnight. The reaction was then concentrated in vacuo and the crude residue redissolved in methanol (1 mL) and cHCl (1 mL) and allowed to stand overnight. The reaction was concentrated again in vacuo and the resulting residue purified by chromatography to afford 13 (61 mg, 84%). $^{13}$C NMR δ 152.4, 151.5, 139.1, 134.8, 122.7, 71.7, 61.1, 60.3, 55.0, 48.4, 48.2.

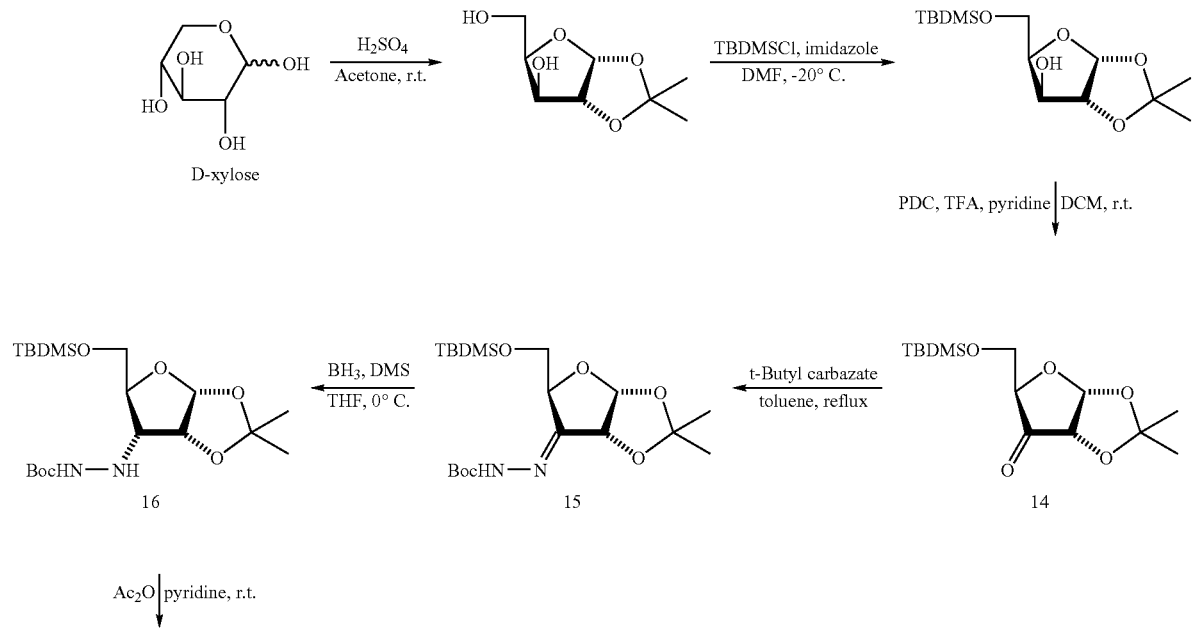

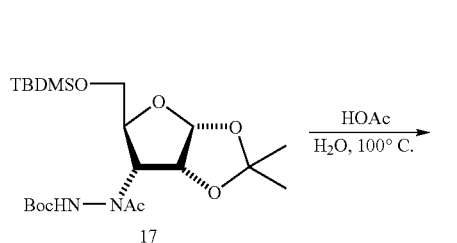
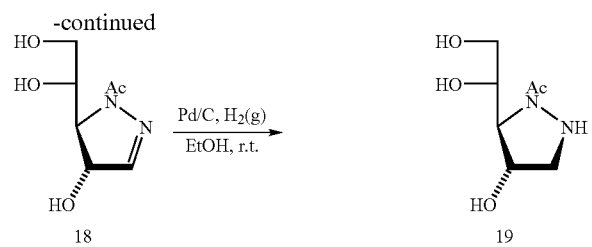

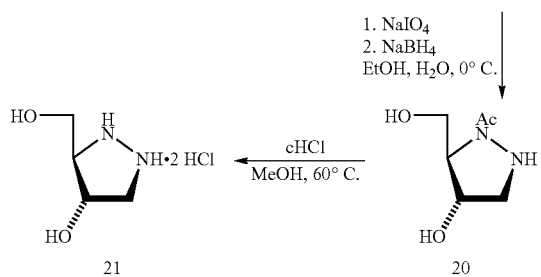

Example 13

5-O-tert-Butyldimethylsilyl-1,2-O-isopropylidene-α-D-erythro-pentofuranos-3-ulose (tert-butoxycarbonyl)hydrazone (15). A toluene (150 mL) solution of 14 (11.5 g, 38 mmol), tert-butyl carbazate (17 g, 128 mmol) and pyridinium p-toluenesulfonate (1.15 g, 4.6 mmol) was stirred overnight at 70° C. On completion the reaction was washed with saturated NaHCO$_3$ and water, dried (MgSO$_4$) and concentrated in vacuo to afford a syrup. Purification by chromatography afforded 15 (12.5 g, 79%) as an oil. $^1$H NMR δ 8.43 (brs, 1H), 5.98 (d, J=4.8 Hz, 1H), 4.90 (dd, J=4.8, 1.5 Hz, 1H), 4.76 (q, J=1.5 Hz, 1H), 3.77 (m, 2H), 1.48 (s, 9H), 1.45 (s, 3H), 1.41 (s, 3H), 0.82 (s, 9H), −0.03 (d, J=5.8 Hz, 6H). $^{13}$C NMR δ 153.5, 152.8, 114.3, 105.7, 82.0, 81.7, 76.2, 66.2, 28.6, 28.0, 27.5, 26.2, 18.5. HRMS (MH$^+$) calc. for C$_{19}$H$_{37}$N$_2$O$_6$Si: 417.2421. Found 417.2398.

Example 14

3-(2-tert-Butoxycarbonylhydrazino)-5-O-tert-butyldimethylsilyl-3-deoxy-1,2-O-isopropylidene-α-D-ribofuranose (16). Borane.DMS complex (15 mL, ~10M, 150 mmol) was added dropwise to a stirred solution of 15 (12.5 g, 30 mmol) at −78° C. under an inert atmosphere. The reaction was allowed to warm to r.t., quenched cautiously with methanol and then the resulting solution concentrated in vacuo. The crude syrup obtained was co-distilled with aliquots of methanol (3×100 mL) to afford 16 (12.5 g, 100%) as an oil which was used in the next step without further purification. $^1$H NMR δ 6.29 (brs, 1H), 5.67 (d, J=3.7 Hz, 1H), 4.62 (t, J=4.3 Hz, 1H), 4.24 (brs, 1H), 3.75 (m, 2H), 3.72 (m, 1H), 1.46 (s, 3H), 1.38 (s, 9H), 1.27 (s, 3H), 0.82 (s, 9H), −0.03 (s, 6H). $^{13}$C NMR δ 156.9, 112.8, 104.6, 80.7, 80.4, 80.2, 65.0, 63.1, 28.7, 27.1, 26.9, 26.3, 18.7. HRMS (MH$^+$) calc. for C$_{19}$H$_{38}$N$_2$O$_6$Si: 418.2499. Found 418.2509.

Example 15

3-(1-Acetyl-2-tert-butoxycarbonylhydrazino-5-O-ter-butyldimethylsilyl-3-deoxy-1,2-O-isopropylidene-α-D-ribofuranose (17). Acetic anhydride (10 mL, excess) was added to a stirred solution of 16 (12.5 g, 30 mmol) in pyridine (30 mL) and the resulting reaction allowed to stir overnight at r.t. On completion the reaction was diluted with chloroform (500 mL) and washed with 10% HCl, water, saturated NaHCO$_3$, brine and then the organic layer was dried (MgSO$_4$), filtered and the filtrate concentrated in vacuo to afford a crude yellow oil. Purification by chromatography afforded 17 (6.5 g, 47%) as a colourless oil. $^1$H NMR δ 7.20 (brs, 1H), 5.75 (d, J=3.8 Hz, 1H), 5.02 (dd, J=9.8, 5.0 Hz, 1H), 4.72 (t, J=4.2 Hz, 1H), 4.04 (dd, J=9.8, 2.2 Hz, 1H), 3.87 (d, J=11.6 Hz, 1H), 3.70 (dd, J=11.6, 3.8 Hz, 1H), 2.09 (s, 3H), 1.55 (s, 3H), 1.42 (s, 9H), 1.28 (s, 3H), 0.84 (s, 9H), −0.03 (r, 6H). $^{13}$C NMR δ 174.5, 155.2, 112.7, 104.7, 82.0, 81.0, 77.2, 62.9, 62.0, 55.0, 28.5, 27.0, 26.7, 26.3, 21.1, 18.7. HRMS (MH$^+$) calc. for C$_{21}$H$_{41}$N$_2$O$_7$Si: 461.2683. Found 461.2704.

Example 16

(3S,4S)-2-Acetyl-3,4-dihydro-3-[(1S)-1,2-dihydroxyethyl]hydroxypyrazole (18). A stirred solution of 17 (2.0 g, 4.3 mmol) in 70% acetic acid (20 mL) was heated at 100° C. overnight. The resulting solution was allowed to cool, diluted with water (100 mL) and the aqueous solution extracted with chloroform (2×100 mL) and then the aqueous layer was concentrated in vacuo to afford a syrup. The product was purified by chromatography to afford 18 (380 mg, 47%) as an oil. $^{13}$C NMR δ 173.1, 150.5, 112.7, 74.7, 69.6, 65.4, 62.4, 21.4. HRMS (MH$^+$) calc. for C$_7$H$_{13}$N$_2$O$_4$: 189.0875. Found 189.0876.

Example 17

(3S,4S)-2-Acetyl-3-[(1S)-1,2-dihydroxyethyl]-4-hydroxypyrazolidine (19). Pearlmans catalyst (200 mg) was suspended in a solution of methanol with (3S,4S)-2-acetyl-1, 5-dihydro-3-[(1S)-1,2-dihydroxyethyl]-4-hydroxy-pyrazole (18) (200 mg, 1.11 mmol) and stirred overnight under an atmosphere of hydrogen. The reaction was filtered through celite and the filtrated concentrated in vacuo to afford a crude oil. The crude product was purified by chromatography to afford 19 (85 mg, 43%) as a colourless oil. $^1$H NMR δ 4.64 (dd, J=5.7, 3.4 Hz, 1H), 3.90 (m, 2H), 3.61 (m, 2H), 3.36 (dd, J=11.7, 6.5 Hz, 1H), 2.71 (dd, J=11.7, 6.0 Hz, 1H), 2.18 (8, 3H). $^{13}$C NMR δ 174.5, 75.4, 72.7, 68.2, 65.2, 56.4, 21.5. HRMS (M$^+$) calc. for C$_7$H$_{14}$N$_2$O$_4$: 190.0953. Found 190.0951.

Example 18

(3R,4S)-2-Acetyl-4-hydroxy-3-hydroxymethyl-pyrazolidine (20). A solution of 19 (80 mg, 0.42 mmol) in ethanol (5 mL) was added dropwise to a stirred solution of sodium periodate (150 mg, 0.7 mmol) in water (5 mL) at such a rate so as to maintain the reaction temperature at 5° C. On completion, sodium borohydride (135 mg, xs) was added portionwise to the resulting suspension at such a rate so as to maintain the reaction temperature at 0° C. and on complete addition the reaction was allowed to warm to r.t. Flash chromatography grade silica was added to the reaction and the resulting suspension was concentrated in vacuo to afford a white solid. The solid was purified by chromatography to afford 20 (51 mg, 76%) as a colourless oil. $^1$H NMR δ 4.43 (dd, J=5.7, 3.3 Hz, 1H), 3.91 (q, J=4.7 Hz, 1H), 3.75 (d, J=4.7 Hz, 1H), 3.31 (m, 1H), 3.28 (dd, J=11.8, 5.7 Hz, 1H), 2.75 (dd, J=11.8, 5.5 Hz, 1H), 2.17 (s, 3H). $^{13}$C NMR δ 173.9, 76.5, 68.2, 62.5, 55.8, 21.7. HRMS (MH$^+$) calc. for C$_6$H$_{13}$N$_2$O$_3$: 161.0926. Found 161.0920.

Example 19

(3R,4S)-4-Hydroxy-3-hydroxymethylpyrazolidine (21). Concentrated HCl (1.5 mL) was added dropwise to a stirred solution of 20 (15 mg, 0.09 mmol) in methanol (1.5 mL) and the resulting reaction kept at 60° C. for 3 h. The reaction was concentrated in vacuo to afford 21 (18 mg, 100%) as its dihydrochloride salt. $^1$H NMR δ 4.60 (q, J=2.4 Hz, 1H), 3.73-3.31 (m, 5H). $^{13}$C NMR δ 72.6, 68.3, 60.2, 54.1.

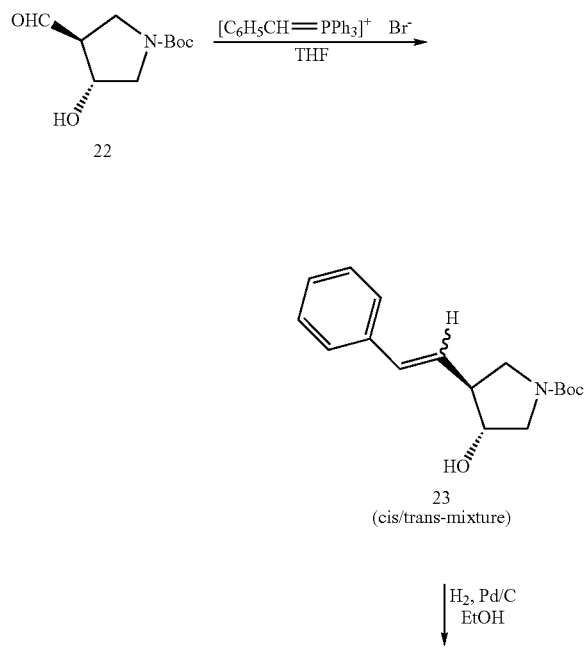

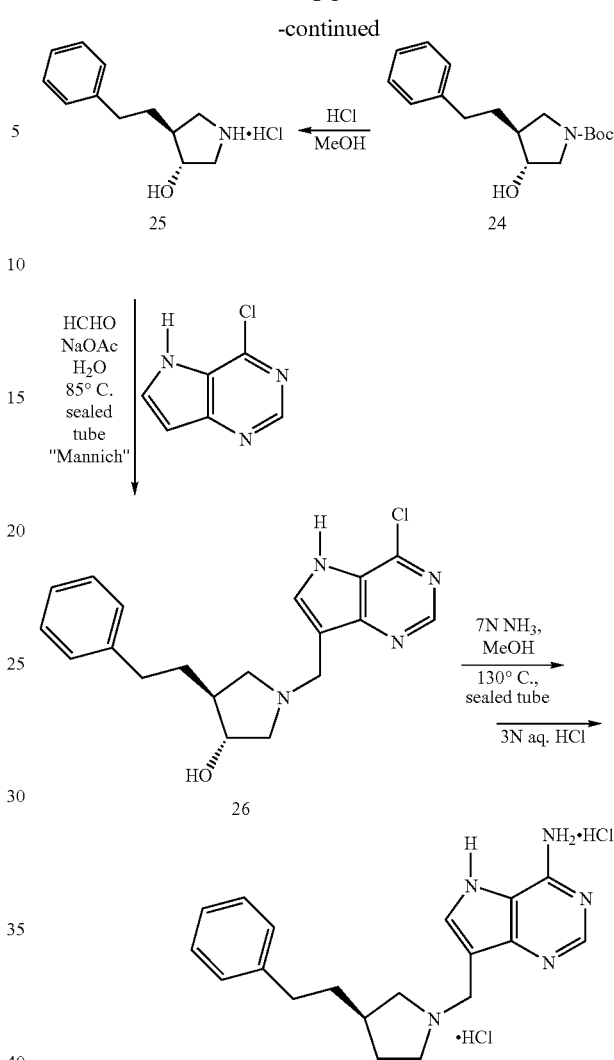

Example 20

N-tert-Butoxycarbonyl-(3R,4S)-3-hydroxy-4-(2-phenylethenyl)pyrrolidine (23) To a suspension of benzyltriphenylphosphonium bromide (1.75 g, 4.97 mmol) in dry THF (10 mL) under argon at 0° C. was added 1.6 M BuLi in THF (2.33 mL, 3.73 mmol) and the deep red solution left stirring without cooling for 10 min. After re-cooling to 0° C., the aldehyde 22 (335 mg, 1.56 mmol) (Gary B. Evans, Richard H. Furneaux, Andrzej Lewandowicz, Vern L. Schramm, and Peter C. Tyler (2003), Synthesis of Second-Generation Transition State Analogues of Human Purine Nucleoside Phosphorylase, *J. Med. Chem.*, in press) in THF (5 mL) was added and the mixture stirred at r.t. for 12 h. The reaction was then quenched with water (1 mL), dichloromethane was added (100 mL) and the organic phase washed with sat. sodium hydrogen carbonate solution (15 mL), then water (15 mL). Drying over magnesium sulfate and concentration in vacuo followed by chromatography afforded a ca. 1:3 cis/trans mixture of 23 as a syrup (290 mg, 64%). $^1$H NMR (300 MHz, CDCl$_3$): δ ppm: trans: 7.28 (m, 5H), 6.49 (d, J=15.9 Hz, 1H), 6.03 (dd, J=15.9 and 8.1 Hz, 1H), 4.11 (m, 1H), 3.67 (m, 2H), 3.32 (m, 2H), 2.83 (m, 1H), 1.46 (s, 9H). cis: 7.27 (m, 5H), 6.58 (d, J=11.6 Hz, 1H), 5.43 (dd, J=11.6 Hz and 10.0 Hz, 1H), 4.11 (m, 1H), 3.65 (m, 2H), 3.21 (m, 2H), 2.88 (m, 1H), 1.44 (s, 9H).

Example 21

N-tert-Butoxycarbonyl-(3R,4S)-3-hydroxy-4-(2-phenylethyl)pyrrolidine (24) To a solution of N-tert-butoxycarbonyl-(3R,4R)-3-hydroxy-4-(2-phenylethenyl)pyrrolidine 23 (290 mg, 1.00 mmol) in ethanol (20 mL) was added 10% Pd/C (250 mg) and the suspension was stirred under an atmosphere of hydrogen for 12 h. After filtration, the solvent was removed in vacuo to give 254 mg (87%) of the title compound as a syrup. $^1$H NMR (300 MHz, CDCl$_3$): δ ppm: 7.10 (m, 5H), 4.00 (m, 1H), 3.47 (m, 2H), 3.07 (m, 2H), 2.67 (m, 2H), 2.04 (m, 1H), 1.83 (m, 1H), 1.54 (m, 1H), 1.45 (s, 9H). $^{13}$C NMR (300 MHz, CDCl$_3$): δ ppm (note that some peaks are doubled due to slow conversion of rotamers): 155.17, 142.03, 128.83, 128.71, 126.37, 79.88, (74.94, 71.26), (53.17, 52.90), (49.90, 49.34), (46.11, 45.52), 34.41, 33.69, 28.91.

Example 22

(3R,4S)-3-Hydroxy-4-(2-phenylethyl)pyrrolidine hydrochloride (25) To a solution of N-tert-butoxycarbonyl-(3R,4R)-3-hydroxy-4-(2-phenylethyl)pyrrolidine 24 (254 mg, 0.87 mmol) in methanol (10 mL) was added conc. HCl (~12 N, 4 mL) and the solution stirred at 40° C. for 30 min. After removal of the solvent in vacuo and azeotroping with toluene, the crude title compound was obtained as a greyish solid (202 mg, 0.89 mmol, 102%).

$^1$H NMR (300 MHz, MeOH-d$_4$): δ ppm: 7.14 (m, 5H), 4.22 (m, 1H), 3.52 (dd, J=11.8 and 7.4 Hz, 1H), 3.39 (dd, J=12.3 and 4.9 Hz, 1H), 3.14 (dd, J=12.3 and 2.8 Hz, 1H), 3.02 (dd, J=11.8 Hz, 1H), 2.71 (m, 2H), 2.20 (m, 1H), 1.84 (m, 1H), 1.62 (m, 1H). $^{13}$C NMR (300 MHz, MeOH-d$_4$): δ ppm: 142.94, 129.93, 129.89, 127.56, 75.56, 52.90, 48.55, 47.28, 35.18, 34.44.

Example 23

(3R,4S)-1-[(9-Deaza-6-chloro-purin-9-yl)methyl]-3-hydroxy-4-(2-phenylethyl)pyrrolidine (26) To a suspension of crude (3R,4R)-3-hydroxy-4-(2-phenylethyl)pyrrolidine hydrochloride 25 (194 mg, 0.85 mmol) and 6-chloro-9-deazapurine (118 mg, 0.76 mmol) in water (2.2 mL) was added 37% aqueous formaldehyde (70 μL, 0.94 mmol) and sodium acetate (70 mg, 0.85 mmol). The mixture was heated to 95° C. in a sealed tube under stirring for 12 h. After cooling, the dark brown slurry was diluted with 1,4-dioxane (3 mL) and the dark brown solution preabsorbed onto silica. Column chromatography afforded the title compound as a cream coloured/brownish film (104 mg, 38%). $^1$H NMR (300 MHz, MeOH-d$_4$): δ ppm: 8.71 (s, 1H), 8.12 (s, 1H), 7.17 (s, 5H), 4.55 (s, 1H), 4.18 (m, 1H), 3.56 (m, 2H), 3.31 (m, 1H), 3.04 (dd, J=11.6 and 7.7 Hz, 1H), 2.64 (m, 2H), 2.21 (m, 1H), 1.87 (m, 1H), 1.61 (m, 1H). $^{13}$C NMR (300 MHz, MeOH-d$_4$): δ ppm: 151.62, 151.35, 145.02, 142.99, 138.11, 129.84, 129.82, 127.46, 126.81, 107.73, 75.68, 61.00, 58.48, 49.51, 47.56, 35.26, 34.88.

Example 24

(3R,4S)-1-[(9-Deazaadenin-9-yl)methyl]-3-hydroxy-4-(2-phenylethyl)pyrrolidine (27) A solution of 7-[(3R,4R)-(3-Hydroxy-4-(2-phenylethyl)pyrrolidin-1-yl)methyl]-4-chloro-pyrrolo[3,2-d]pyrimidine 26 (70 mg, 0.196 mmol) in 7 N methanolic ammonia (4 mL) was heated in a sealed tube at 130° C. under stirring for 3 h. After cooling, the solvent was removed in vacuo. The residue was taken up in methanol and the crude material preabsorbed onto silica. The material obtained after column chromatography was treated with 3 N aqueous HCl (4 mL) at 40° C. for 1 h. Lyophilisation afforded 31 mg (39%) of the title compound as a cream coloured solid. $^1$H NMR (300 MHz, D$_2$O): δ ppm: 8.40 (s, 1H), 7.83 (s, 1H), 7.26 (m, 5H), 4.33 (m, 4H), 4.07 (m, 1H), 3.80 (m, 2H), 2.75 (m, 2H), 2.37 (m, 1H), 1.90 (m, 1H), 1.66 (m, 1H). $^{13}$C NMR (300 MHz, D$_2$O): δ ppm (note that some peaks are doubled due to slow conversion of rotamers): 149.54, 144.47, 142.40, 133.05, 129.05, 128.85, 126.51, 113.64, 103.48, (74.87, 72.96), (55.34, 54.87), (52.59, 52.09), (45.96, 43.65), 33.30, 32.94, 32.33. ES-MS: m/z for C$_{19}$H$_{23}$N$_5$O: (M+H)$^+$: 338.1979; calc. 338.4326.

Scheme 9

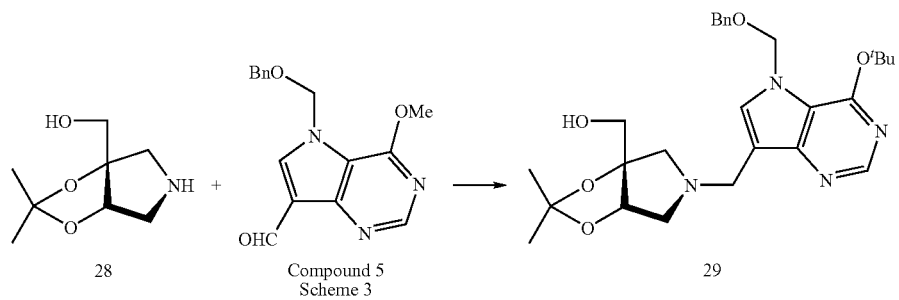

28     Compound 5 Scheme 3     29

-continued

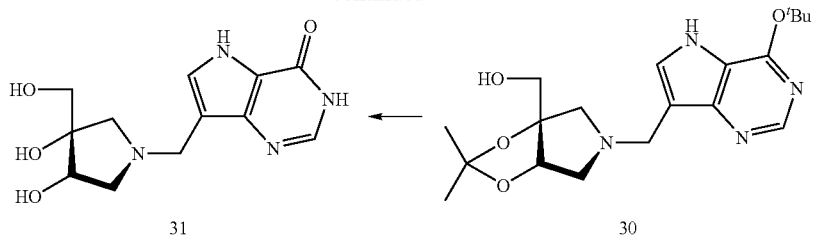

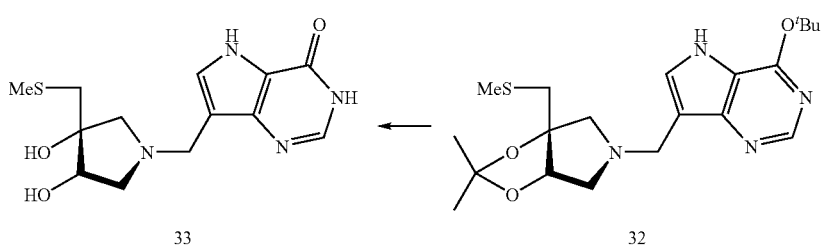

Example 25

(3S,4S)-1-[(7-N-Benzyloxymethyl-6-O-tert-butyl-9-deazahypoxanthin-9-yl)methyl]-3,4-dihydroxy-4-hydroxymethyl-3, isopropylidenepyrrolidine (29). A solution of amine 28 (Bols, M. *Tetrahedron Lett.* 1996, 37, 2097-2100) (0.50 g, 2.89 mmol) and aldehyde (5, Scheme 3) (1.0 g, 2.95 mmol) in 1,2-dichloroethane (50 mL) was stirred with sodium triacetoxyborohydride (1.1 g, 5.2 mmol) for 1 h and then was washed with aq NaHCO$_3$, dried and concentrated to dryness. Chromatography afforded title compound 29 (1.16 g, 2.34 mmol, 80%) as a syrup. $^{13}$C NMR (CDCl$_3$) δ 156.2, 150.3 (C), 150.0 (CH), 137.5 (C), 131.8, 128.8, 128.2, 127.8 (CH), 117.1, 114.6, 113.0, 91.7, 83.2 (C), 82.4 (CH), 77.3, 70.2, 65.7, 62.1, 60.5, 48.4 (CH$_2$), 29.1, 28.3 (CH$_3$).

Example 26

(3S,4S)-1-[(6-O-tert-Butyl-9-deazahypoxanthin-9-yl)methyl]-3,4-dihydroxy-4-hydroxymethyl-3,4-O-Isopropylidenepyrrolidine (30). A solution of 29 (1.1 g, 2.21 mmol) in ethanol (30 mL) was stirred under hydrogen in the presence of 10% Pd/C (0.25 g). After 16 h additional catalyst was added and after 24 h the solids and solvent were removed. Chromatography of the residue afforded title compound 30 (0.35 g, 0.93 mmol, 42%) as a syrup. $^{13}$C NMR (CD$_3$OD) δ 157.7 (C), 150.2 (CH), 149.8 (C), 131.0 (CH), 118.2, 113.7, 112.9, 93.1, 83.9 (C), 83.5 (CH), 66.4, 62.7, 61.0, 48.9 (CH$_2$), 29.4, 28.2 (CH$_3$).

Example 27

(3S,4S)-1-[(9-deazahypoxanthin-9-yl)methyl]-3,4-dihydroxy-4-hydroxymethylpyrrolidine (31). A solution of 30 (0.15 g, 0.399 mmol) in methanol (2.5 mL) and cHCl (2.5 mL) was allowed to stand for 1 h and then concentrated to dryness. Chromatography of the residue [(CH$_2$Cl$_2$/MeOH/aq NH$_3$ 10:6:1] afforded title compound 31 (0.095 g, 0.34 mmol, 85%) as a white solid. $^{13}$C NMR (D$_2$O/DCl) (at 85° C.) δ 153.8 (C), 144.7 (CH), 138.0 (C), 132.8 (CH), 118.5, 103.8, 78.8 (C), 70.1 (CH), 63.5, 59.5, 57.3, 49.3 (CH$_2$).

Example 28

(3S,4R)-1-[(9-deazahypoxanthin-9-yl)methyl]-3,4-dihydroxy-4-methylthiomethylpyrrolidine (33). Ethyldiisopropylamine (0.2 mL) was added to a suspension of 30 (0.14 g) in dichloromethane (5 mL) followed by methanesulfonyl chloride (0.045 mL) and the mixture was stirred for 1 h. The resulting solution was processed normally and the crude product, in DMF (3 mL), was treated with sodium thiomethoxide (0.13 g) and the resulting mixture was heated at 90° C. for 4 h and then partitioned between toluene and water. The organic phase was washed with water, dried and concentrated. Chromatography of the residue afforded 32 (0.075 g). A solution of this material in methanol (4 mL) and cHCl (4 mL) was allowed to stand for 1 h, and then concentrated to dryness to give 33.HCl (0.04 g, 62%) as a white solid. $^{13}$C NMR (D$_2$O) δ 153.4 (C), 145.0 (CH), 135.5 (C), 133.1 (CH), 118.6, 102.9, 79.2 (C), 71.9 (CH), 60.6, 56.7, 48.3, 39.2 (CH$_2$), 17.1 (CH$_3$).

Scheme 10

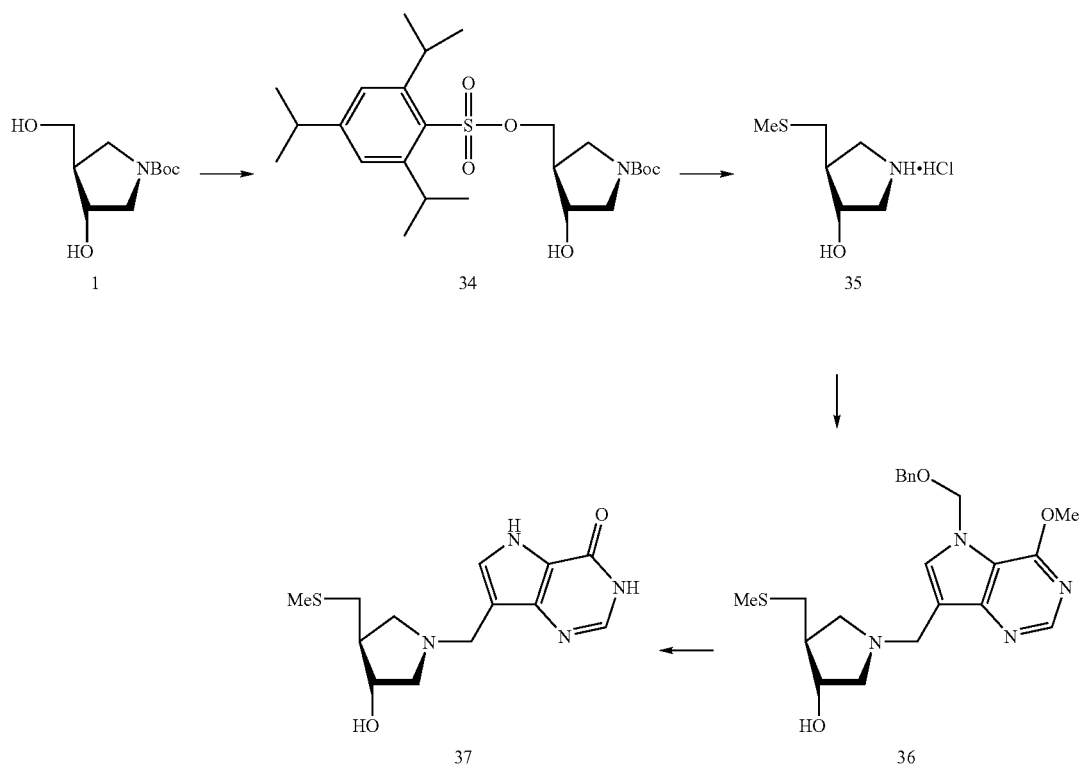

Example 29

(3R,4S)-1-[(9-Deazahypoxanthin-9-yl)methyl]-3-hydroxy-4-(methylthiomethyl)pyrrolidine (37). 2,4,6-Triisopropylbenzenesulfonyl chloride (3.0 g) was added to a solution of 1 (1.0 g) in pyridine (20 mL) and the solution was stirred for 16 h, then was warmed to 60° C. for 1 h. Chloroform was added and the solution was washed with water, 2M aq HCl, and aq NaHCO$_3$. Normal processing and chromatography gave 1.125 g of 34 as a colourless glass. A solution of 0.45 g of this material in DMF (5 mL) was treated with sodium thiomethoxide (0.2 g) and the mixture was stirred for 0.5 h. Toluene was added and the reaction was processed normally to give 0.115 g of crude material. A solution of this material in dichloromethane (5 mL) was treated with 4M HCl in dioxane (3 mL). After 1 h the solution was concentrated to dryness. The solid residue of 35 was dissolved in methanol (3 mL) containing 7-N-benzyloxymethyl-9-deaza-6-O-methylhypoxanthine-9-carbaldehyde (0.18 g), and sodium cyanoborohydride (0.088 g) was added. The mixture was stirred for 3 d. Chloroform was added and the mixture was processed normally. Chromatography then afforded 36 (0.178 g). This material in cHCl (10 mL) was heated under reflux for 1 h, then the solution was concentrated to dryness. The residue was treated with methanol/25% aq NH$_3$ (1:1) for 1 h and then concentrated to dryness. Chromatography afforded a solid material. This was dissolved in aq HCl and concentrated. Trituration of the residue with ethanol gave 37.HCl (0.048 g) as a hygroscopic white solid. $^{13}$C NMR (D$_2$O at 85° C.) δ 154.6 (C), 144.5 (CH), 140.6 (C), 132.6 (CH), 118.6, 104.6 (C), 73.3 (CH), 59.3, 56.3, 48.0 (CH$_2$), 45.7 (CH), 34.7 (CH$_2$), 15.2 (CH$_3$).

Scheme 11

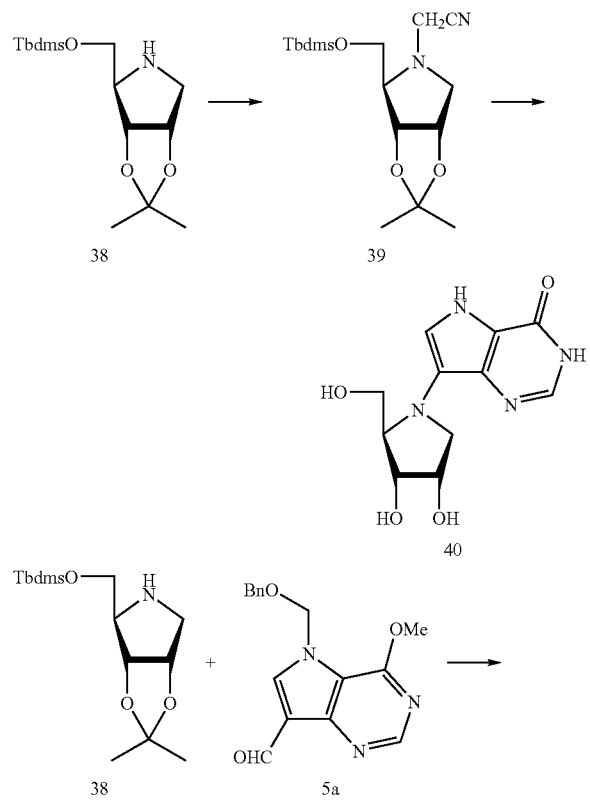

-continued

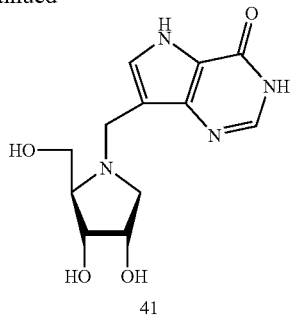

41

Example 30

5-O-tert-Butyldimethylsilyl-N-cyanomethyl-1,4-dideoxy-1,4-imino-2,3-O-isopropylidene-D-ribitol (39). Bromoacetonitrile (1.46 mL, 20.9 mmol) and ethyldiisopropylamine (5.46 mL, 56.9 mmol) were added to a solution of 38 (Horenstein, B A.; Zabinski, R. F.; Schramm, V. L. *Tetrahedron Lett.* 1993, 34, 7213-7216) (3.0 g, 10.45 mmol) in acetonitrile (20 mL). After 1 h, the solution was concentrated to dryness and chromatography of the residue afforded title compound 39 as a syrup (3.4 g, 10.4 mmol, 99%). $^1$H NMR δ 4.58 (dt, J=6.4, 4.3 Hz, 1H), 4.20 (dd, J=6.8, 4.2 Hz, 1H), 3.88 (d, J=17 Hz, 1H), 3.79 (dd, J=10.9, 3.0 Hz, 1H), 3.58 (m, 1H), 3.56 (d, J=17 Hz, 1H), 3.19 (dd, J=9.8, 6.1 Hz, 1H), 2.85 (m, 1H), 2.75 (dd, J=9.8, 4.3 Hz, 1H), 1.44 (s, 3H), 1.23 (s, 3H), 0.82 (s, 9H), 0.09 (s, 3H), 0.08 (s, 3H); $^{13}$C NMR δ 115.6, 113.6 (C), 82.2, 78.3, 68.6 (CH), 64.7, 59.3, 41.0 (CH$_2$), 27.6, 26.2, 25.6 (CH$_3$), 18.5 (C). HRMS (MH$^+$) calc. For C$_{16}$H$_{31}$N$_2$O$_3$Si: 327.2104. Found: 327.2097.

Example 31

N-(9-Deazahypoxanthin-9-yl)-1,4-dideoxy-1,4-imino-D-ribitol hydrochloride (40.HCl). The N-cyanomethyl derivative 39 (0.5 g, 1.53 mmol) was converted into the title compound by the same sequence of reactions described previously in the preparation of Immucillin-H (Evans, G. B.; Furneaux, R. H.; Gainsford, G. J.; Schramm, V. L.; Tyler, P. C. *Tetrahedron* 2000, 56, 3053-3062) to give 40.HCl as an amorphous powder (0.07 g, 0.23 mmol, 15%). $^1$H NMR (D$_2$O) δ 8.24 (s, 1H), 7.71 (s, 1H), 4.43 (m, 1H), 4.29-4.17 (m, 2H), 3.96 (m, 1H), 3.82-3.71 (m, 3H); $^{13}$C NMR δ 154.2 (C), 144.3 (CH), 133.0 (C), 124.0 (CH), 117.8, 115.9 (C), 73.4, 70.4, 68.9 (CH), 62.9, 56.1 (CH$_2$). HRMS (M$^+$) calc. For C$_{11}$H$_{16}$N$_4$O$_4$: 267.1093. Found: 267.1101.

Example 32.1

7-N-Benzyloxymethyl-9-deaza-9-formyl-6-O-methylhypoxanthine (5a). A solution of 7-N-benzyloxymethyl-9-bromo-9-deaza-6-O-methylhypoxanthine (G. B. Evans et al J. Org. Chem. 2001, 66, 5723-5730) (1.0 g, 2.87 mmol) in anisole (10 mL) and ether (25 mL) was cooled to −70° C. and n-butyllithium (2.4 mL, 1.2 M) was added to the resulting suspension. After 10 min, dry N,N-dimethylformamide (1:1 mL, 14.2 mmol) was added to the clear solution which was stirred at −70° C. for 30 min and then quenched with water. Normal processing afforded a solid, which after trituration with ethanol gave title compound as a white solid (0.67 g, 2.26 mmol, 78%) with m.p. 100-101° C. $^1$H NMR d 10.30 (s, 1H), 8.67 (s, 1H), 8.00 (s, 1H), 7.35-7.21 (m, 5H), 5.77 (s, 2H), 4.55 (s, 2H), 4.14 (s, 3H); $^{13}$C NMR d 184.7 (CH), 157.0 (C), 153.0 (CH), 150.0 (C), 136.9 (CH), 136.5 (C), 129.0, 128.7, 128.1 (CH), 118.6, 116.7 (C), 78.3, 71.4 (CH2), 54.3 (CH3). HRMS (MH+) calcd for C$_{19}$H$_{21}$N$_3$O$_3$ 340.1661 found: 340.1652.

Example 32.2

N-9-Deazahypoxanthin-9-yl)methyl-1,4-dideoxy-1,4-imino-D-ribitol hydrochloride (41.HCl). The aldehyde (5a) (114 mg, 0.38 mmol) was added to a solution of 38 (Horenstein, B. A.; Zabinski, R. F.; Schramm, V. L. *Tetrahedron Lett.* 1993, 34, 7213-7216) (100 mg, 0.35 mmol) in methanol (1.5 mL), THF (0.5 mL) and acetic acid (100 μL) and the mixture was stirred for 10 min. Sodium cyanoborohydride (88 mg, 1.4 mmol) was added and the solution was stirred for 4 h, then partitioned between chloroform and aq. NaHCO$_3$. The organic layer was dried and concentrated to dryness. Chromatography of the residue afforded, presumably, N-(7-N-benzyloxymethyl-9-deaza-6-methylhypoxanthin-9-yl)methyl-5-O-tert-butyldimethylsilyl-1,4-dideoxy-1,4-imino-2,3-O-isopropylidene-D-ribitol as a syrup (175 mg, 0.31 mmol, 88%). A solution of this material in ethanol (5 mL) was stirred with 10% Pd/C (100 mg) in a hydrogen atmosphere for 16 h. The solids and solvent were removed and chromatography of the residue afforded a syrup (129 mg) which was dissolved in methanol (5 mL) and conc. HCl (5 mL) and the solution was heated under reflux for 2 h. The solution was concentrated to dryness and the residue redissolved in water and lyophilized to give title compound 41.HCl as a powder (80 mg, 0.25 mmol, 80%). $^1$H NMR (D$_2$O) δ 8.57 (m, 1H), 7.78 (s, 1H), 4.66 (s, 1H), 4.56 (s, 1H), 4.29 (m, 1H), 4.13 (m, 1H), 3.76 (m, 2H), 3.61 (m, 2H), 3.34 (dd, J=13.0, 3.4 Hz, 1H); $^{13}$C NMR δ 153.6 (C), 144.8 (CH), 136.7 (C), 133.2 (CH), 118.5, 103.3 (C), 71.3, 70.3, 68.9 (CH), 57.4, 57.1, 50.1 (CH$_2$). HRMS (M$^+$) calc. For C$_{12}$H$_{17}$N$_4$O$_4$: 281.1250. Found: 281.1260.

Scheme 12

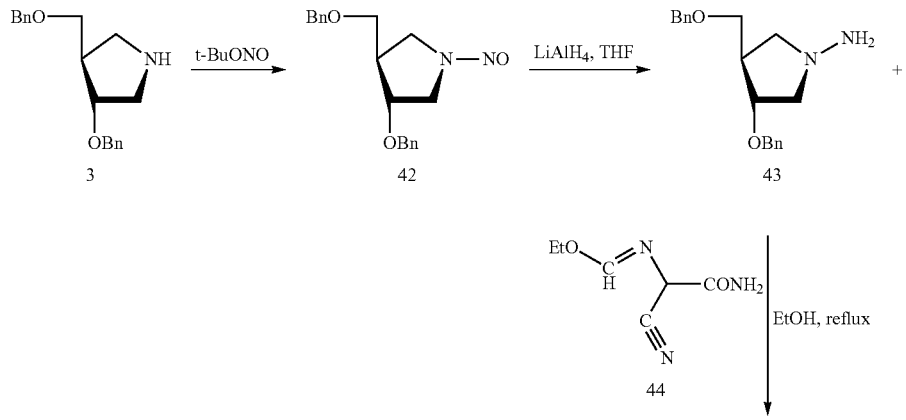

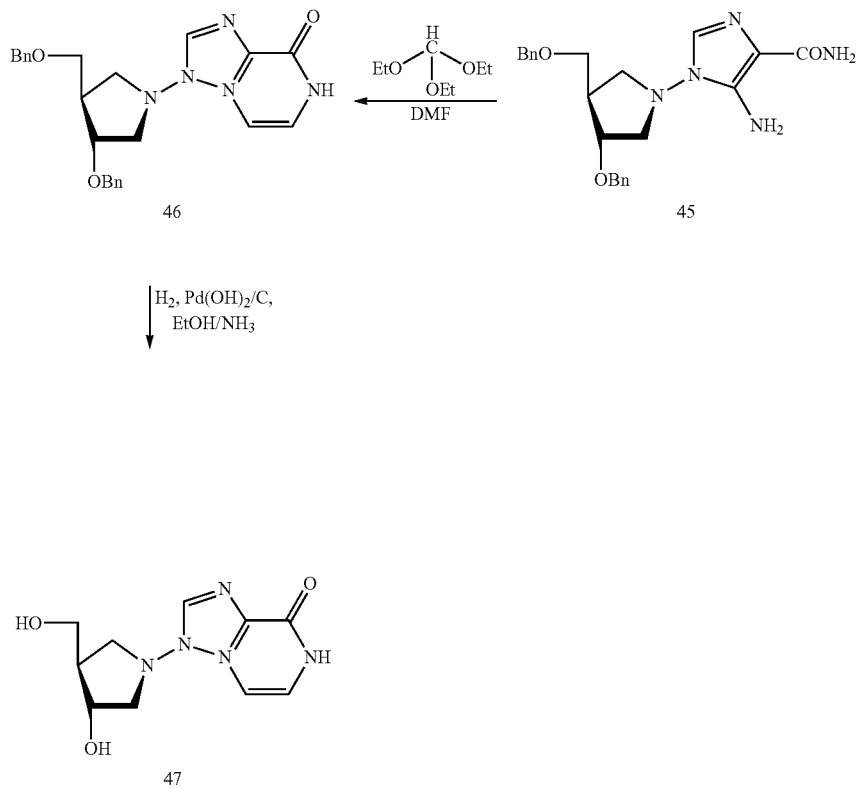

Example 33

(3R,4R)-3-Hydroxy hydroxymethyl-1-(hypoxanthin-9-yl) pyrrolidine (47). tert-Butyl nitrite (3.5 mL, 30 mmol, 4 eq.) was added to a solution of the free base of 3 (2.25 g, 7.5 mmol) in dry THF (30 mL) and the reaction mixture was stirred at ambient temperature for 3 days. The solution was concentrated to dryness. Chromatography gave the N-nitroso compound 42 as a colorless syrup (2.05 g, 83%). A solution of 42 (1.0 g, 3.1 mmol) in dry THF (20 mL) was cooled to 0° C. under argon atmosphere and lithium aluminum hydride (1 g, 26.3 mmol) was added slowly. The mixture was stirred at room temperature for 6 h, then quenched carefully with a 15% solution of NaOH (25 mL) followed by water (10 mL). The mixture was extracted twice with chloroform, washed with aq NaHCO$_3$ and dried and concentrated to dryness. Chromatography (chloroform:ethyl acetate:methanol, 5:2:1) afforded hydrazine 43 (0.41 g, 43%) as a syrup. Formimidate 44 (Watson, A. A *J. Org. Chem.* 1974, 39, 2911-2916) (0.224 g, 1.44 mmol, 1.2 eq.) was added to a solution of 43 (0.375 g, 1.2 mmol) in ethanol (1.5 mL) and the reaction mixture was heated under reflux for 10 min, then allowed to cool. The solution was concentrated to dryness. Chromatography (chloroform:ethyl acetate:methanol, 5:2:1) gave the imidazole 45 as a light brown gum (0.155 g, 31%). A solution of 45 (77 mg, 0.183 mmol) in dry MeOH (1 mL) was treated with 5 M aq HCl (36.5 mL, 0.183 mmol). The solvent was removed to leave the hydrochloride salt as a brown gum. DMF (1.5 mL) was added followed by triethyl orthoformate (0.304 mL, 1.83 mmol, 10 eq.) and the reaction mixture was heated at 120° C. for 30 min. After cooling the solvent was removed in vacuo. The residue was purified by column chromatography on silica gel (chloroform:ethyl acetate:methanol, 5:2:0.5) to afford the hypoxanthine 46 (49 mg, 62%) as a gum. Palladium hydroxide on carbon (20 mg, 20% Pd) was added to a solution of 46 (41 mg, 0.095 mmol) in ethanol (3 mL) and 25% aqueous ammonia (1 mL). The reaction mixture was stirred under hydrogen at ambient temperature and pressure for 3 h. Then the catalyst was filtered off and washed with ethanol (1.5 mL). The solution was concentrated to dryness and chromatography of the residue (dichloromethane:methanol:aq. ammonia, 7:2:0.5) furnished the title compound 47 (21 mg, 88%) as a white solid. $^1$H NMR (CD$_3$OD) δ 8.17 (s, 1H), 8.07 (s, 1H), 4.26 (m, 1H), 3.85-3.64 (m, 4H), 3.48-3.43 (m, 2H), 2.49-2.41 (m, 1H); $^{13}$C NMR δ 159.3 (C), 149.7 (C), 146.7 (CH), 142.3 (CH), 124.7 (C), 72.7 (CH), 63.7, 63.6, 58.4 (CH$_2$), 50.2 (CH). M/Z calculated for C$_{10}$H$_{13}$N$_5$O$_3$ (MH$^+$): 252.109. Found: 252.108.

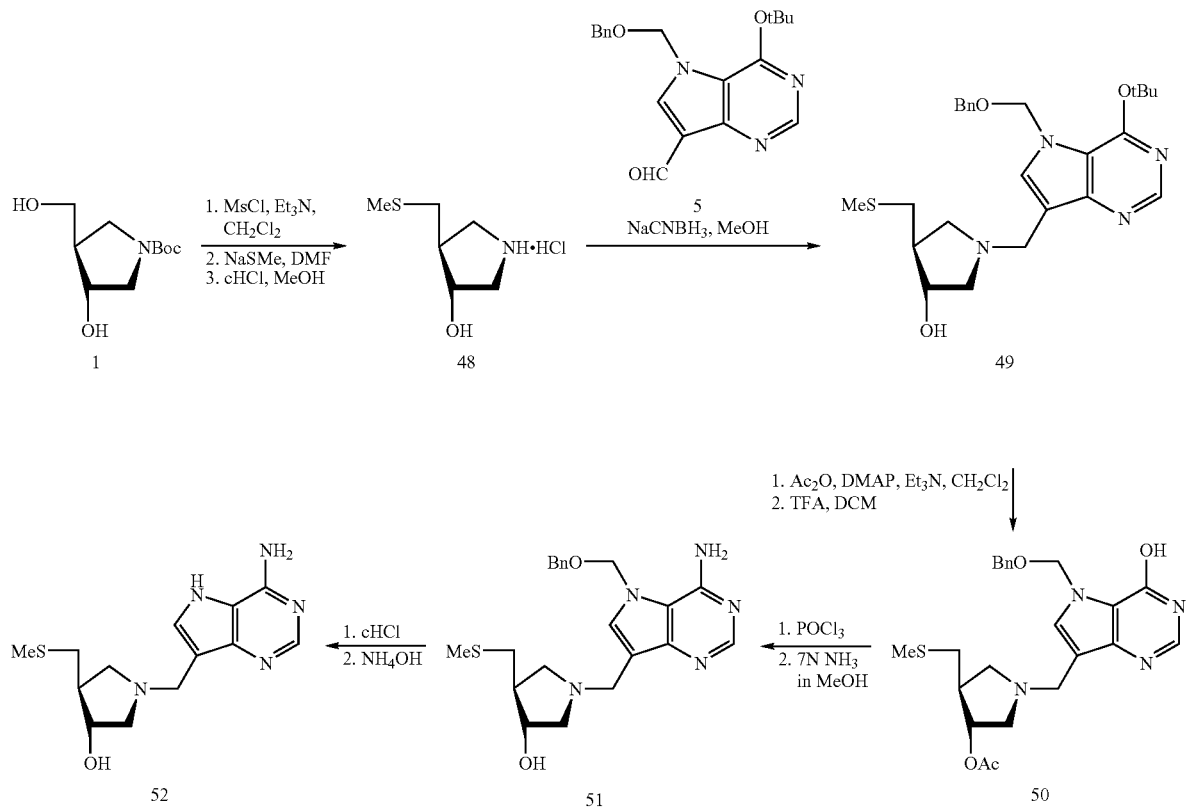

Scheme 13

Example 34

(3R,4S)-3-Hydroxy-4-(methylthiomethyl)pyrrolidine hydrochloride (48). Methanesulfonyl chloride (180 μL, 23 mmol) was added dropwise to a CH$_2$Cl$_2$ solution of triethylamine (400 μL, 29 mmol) and (3R,4R)-1-tert-butoxycarbonyl-3-hydroxy-4-(hydroxymethyl)pyrrolidine (1) (2 g, 9.2 mmol) at 0° C. and the resulting solution allowed to warm to room temperature. The reaction was diluted with CH$_2$Cl$_2$, washed with water, brine, dried (MgSO$_4$) and concentrated in vacuo. The resulting residue was purified by silica gel flash chromatography to afford (3R,4R)-1-tert-butoxycarbonyl-3-hydroxy-4-(mesyloxymethyl)pyrrolidine (900 mg) as an oil. Without further purification the product was dissolved in DMF (10 mL) and stirred with sodium thiomethoxide (400 mg, 5.7 mmol) at room temp. overnight. The reaction was diluted with toluene washed with water, brine, dried (MgSO$_4$) and concentrated in vacuo. The resulting residue was purified by silica gel flash chromatography to afford (3R,4S)-1-tert-butoxycarbonyl-3-hydroxy-4-(methylthiomethyl)pyrrolidine (600 mg, 2.4 mmol) as a syrup, which was not further characterised. (3R,4S)-1-tert-Butoxycarbonyl-3-hydroxy-4-(methylthio)pyrrolidine was dissolved in MeOH (5.0 mL) and cHCl (1.0 mL) and concentrated in vacuo to afford (3R,4S)-3-hydroxy-4-(methylthiomethyl)pyrrolidine hydrochloride (48) as a syrup (442 mg, 26% overall yield for three steps). $^{13}$C NMR (D$_2$O) δ 73.5, 51.5, 48.6, 45.2, 34.3, 14.9.

Example 35

(3R,4S)-1-[(6-tert-Butoxy-7-benzyloxymethyl-9-deazapurin-9-yl)methyl]-3-hydroxy-4-(methylthiomethyl)pyrrolidine (49). Sodium cyanoborohydride (200 mg, 3.2 mmol) was added to a stirred solution of 6 (800 mg, 2.32 mmol) and 48 (550 mg, 3.00 mmol) in methanol (10 mL) and the mixture was stirred overnight at room temperature. The crude reaction was adsorbed onto silica, dry loaded onto a silica gel flash chromatography column and eluted to afford 49 (1.10 g, 78%) as a solid. $^1$H NMR (CDCl$_3$) δ 8.48 (a, 1H), 7.54 (s, 1H), 7.33-7.23 (m, 5H), 5.75 (s, 2H), 4.50 (s, 2H), 4.12 (m, 1H), 4.02 (s, 2H), 3.30 (dd, J=9.9, 7.5 Hz, 1H), 2.95 (m, 2H), 2.64 (dd, J=12.7, 7.1 Hz, 1H), 2.52-2.38 (m, 3H), 2.07 (s, 3H), 1.70 (s, 9H). $^{13}$C NMR (CDCl$_3$) δ 156.4, 150.3, 150.3, 137.5, 133.3, 128.8, 128.2, 127.8, 117.1, 111.7, 83.5, 77.5, 76.1, 70.4, 61.4, 58.2, 48.8, 47.4, 37.3, 29.0, 16.0.

Example 36

(3R,4S)-3-Acetoxy-1-[(7-benzyloxymethyl-9-deazahypoxanthin-9-yl)methyl]-4-(methylthiomethyl)pyrrolidine (50). Acetic anhydride (1 mL, xs) was added dropwise to a solution of compound 49 (1.1 g, 2.3 mmol), DMAP (30 mg, cat.), and Et$_3$N (2 mL, xs) in CH$_2$Cl$_2$ (20 mL) at room temp. After 15 min. the reaction was diluted with CH$_2$Cl$_2$, washed with satd. NaHCO$_3$, water, brine, dried (MgSO$_4$) and concentrated in vacuo. The resulting residue was purified by flash chromatography on silica gel to afford the product (1.35 g) as a syrup. TFA (5 mL) was added dropwise to a solution of the syrup in CH$_2$Cl$_2$ (20 mL) at room temp. and concentrated in vacuo. The resulting residue was redissolved in CH$_2$Cl$_2$ and washed with satd. NaHCO$_3$, water and brine, dried (MgSO$_4$) and concentrated in vacuo to afford (3R,4S)-3-acetoxy-1-[(7-benzyloxymethyl-9-deazahypoxanthin-9-yl)methyl]-4-(methylthiomethyl)pyrrolidine (50) (800 mg, 76%) as a foam. $^1$H NMR (CDCl$_3$) δ 7.80 (s, 1H), 7.65 (s, 1H), 7.25-7.20 (m, 5H), 5.82 (s, 2H), 5.11 (brs, 1H), 4.56 (s, 2H), 4.47 (s, 2H), 3.80-3.59 (m, 3H), 3.32 (brs, 1H), 2.80-2.69 (m, 2H), 2.57 (dd, J=13.0, 8.3 Hz, 1H), 2.07 (s, 3H), 2.05 (s, 3H). $^{13}$C NMR (CDCl$_3$) δ 170.7, 155.4, 145.8, 143.3, 137.2, 134.2, 128.8, 128.3, 128.1, 118.1, 106.9, 77.4, 75.7, 71.2, 57.0, 55.8, 48.1, 43.5, 35.0, 21.0, 16.1. HRMS (MH$^+$) calc for C$_{23}$H$_{29}$N$_4$O$_4$S: 457.1910. Found 457.2412.

Example 37

(3R,4S)-1-[(7-benzyloxymethyl-9-deazaadenin-9-yl)methyl]-3-hydroxy-4-(methylthiomethyl)pyrrolidine (51). Amine 50 (800 mg, 1.75 mmol) was dissolved in POCl$_3$ and heated at reflux for 1 h. The resulting solution was concentrated in vacuo and codistilled with toluene (×2) to afford a solid residue. Without further purification the product from the previous reaction was redissolved in 7 N NH$_3$ in MeOH (15 mL) and heated in a sealed tube at 110° C. overnight. The reaction was concentrated in vacuo and the resulting residue purified by flash chromatography on silica gel to afford (3R,4S)-1-[(7-benzyloxymethyl-9-deazaadenin-9-yl)methyl]-3-hydroxy-4-(methylthiomethyl)pyrrolidine (51) (500 mg, 69%) as a syrup. $^1$H NMR (d$_4$-MeOH) δ 8.24 (s, 1H), 7.85 (s, 1H), 7.29-7.26 (m, 5H), 5.74 (s, 2H), 4.63 (s, 2H), 4.43 (s, 2H), 4.26-4.22 (m, 1H), 3.70 (dd, J=11.4, 6.9 Hz, 1H), 3.49 (dd, J=12.1, 5.6 Hz, 1H), 3.29 (dd, J=12.3, 3.3 Hz, 1H), 3.16 (dd, J=11.4, 6.1 Hz, 1H), 2.76-2.67 (m, 1H), 2.50-2.44 (m, 2H), 2.07 (s, 3H). $^{13}$C NMR (CDCl$_3$) δ 153.4, 153.0, 149.9, 138.1, 137.0, 130.0, 129.7, 129.3, 116.5, 106.5, 79.5, 75.0, 72.3, 60.9, 57.8, 50.1, 47.6, 36.6, 16.0.

Example 38

(3R,4S)-1-[(9-Deazaadenin-9-yl)methyl]-3-hydroxy-4-(methylthiomethyl)pyrrolidine (52). Amine (51) (150 mg, 0.37 mmol) was dissolved cHCl (5 mL) and the resulting solution heated under reflux for 90 min. The reaction was cooled to room temperature, diluted with water (50 mL) and washed with CHCl$_3$ (×2), and the aqueous layer concentrated in vacuo, followed by codistillation with water (×2). The resulting residue was redissolved in NH$_4$OH, concentrated in vacuo, and the residue purified by flash chromatography on silica gel to afford (3R,4S)-1-[(deazaadenin-9-yl)methyl]-3-hydroxy-4-(methylthiomethyl)pyrrolidine (52) (69 mg, 65%) as a solid. M.p. 108-110° C. $^1$H NMR (D$_2$O) δ 7.96 (s, 1H), 7.31 (s, 1H), 4.00-3.95 (m, 1H), 3.74 (s, 2H), 3.05 (dd, J=10.5, 7.9 Hz, 1H), 2.88 (dd, J=11.1, 6.2 Hz, 1H), 2.71 (dd, J=11.1, 4.0 Hz, 1H), 2.49 (dd, J=13.0, 6.7 Hz, 1H), 2.40-2.24 (m, 2H), 2.16-2.13 (m, 1H), 1.93 (s, 3H). $^{13}$C NMR (D$_2$O) δ 150.5, 150.1, 145.4, 130.4, 113.6, 108.33, 75.0, 59.8, 56.6, 47.4, 45.9, 35.9, 14.8. HRMS (MH$^+$) calc for C$_{13}$H$_{20}$N$_5$OS: 294.1389. Found 294.1394. Anal. Calc. for C$_{13}$H$_{19}$N$_5$OS.4/3H$_2$O C, 49.19; H, 6.88; N, 22.06; S, 10.10. Found C, 49.86; H, 6.58; N, 21.63; S, 9.74.

Scheme 14

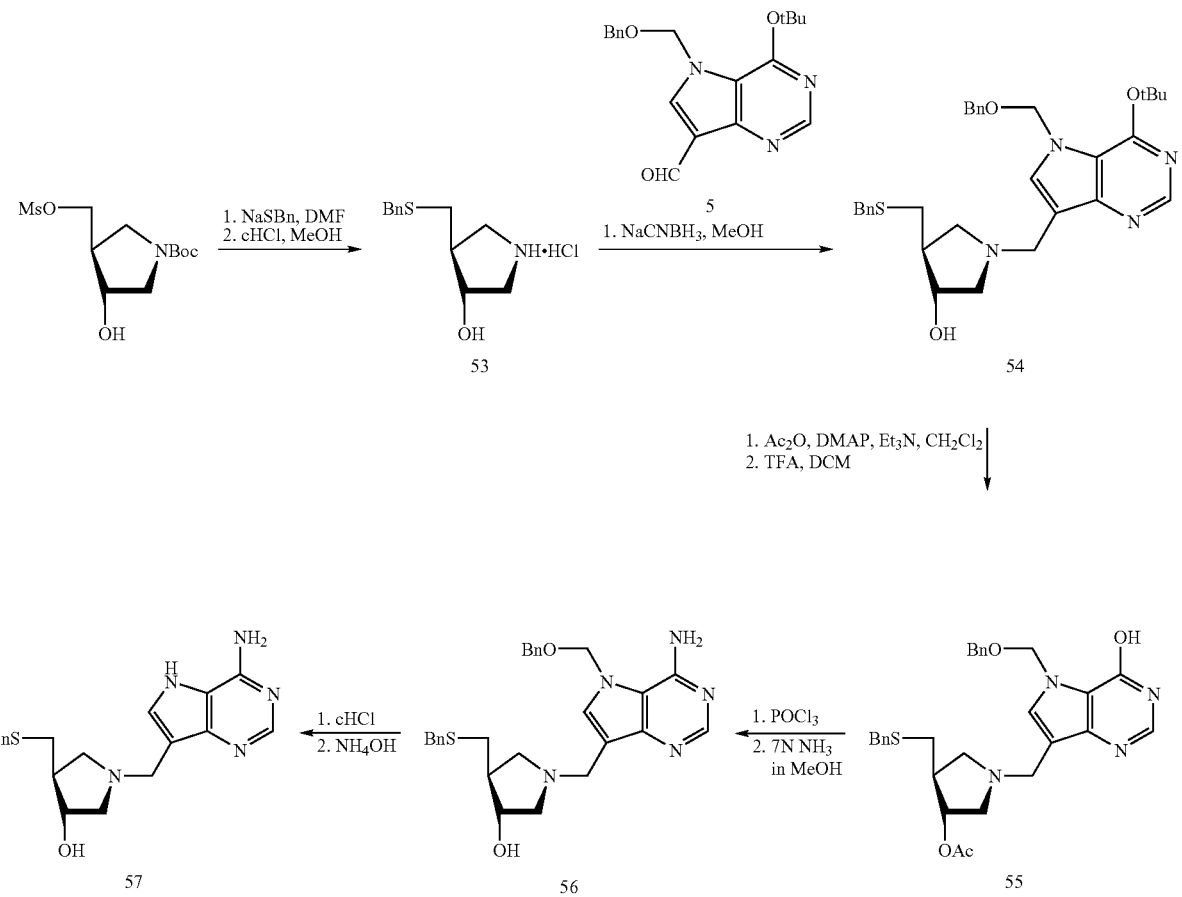

Example 39

(3R,4S)-3-Hydroxy-4-(benzylthiomethyl)pyrrolidine hydrochloride (53). (3R,4R)-1-tert-Butoxycarbonyl-3-hydroxy-4-(mesyloxymethyl)pyrrolidine (see Example 34, 1.10 g, 3.7 mmol) was dissolved in DMF (2 mL) and added dropwise to a solution of benzyl mercaptan (870 μL, 7.4 mmol) and NaH (270 mg, 60% oil dispersion, 6.8 mmol) In DMF (10 mL) and stirred at room temp. for 1 h. The reaction was diluted with toluene, washed with water then brine, dried ($MgSO_4$) and concentrated in vacuo. The resulting residue was purified by silica gel flash chromatography to afford (3R,4S)-1-tert-butoxycarbonyl-3-hydroxy-4-(benzylthiomethyl)pyrrolidine as a syrup. Without further characterisation, the product was dissolved in MeOH (5.0 mL) and cHCl (1.0 mL) and concentrated in vacuo to afford (3R,4S)-3-hydroxy-4-(benzylthiomethyl)pyrrolidine hydrochloride (53) as a syrup (730 mg, 76% overall yield for two steps). $^1$H NMR ($D_2O$) δ 7.40-7.27 (m, 5H), 4.26-4.22 (m, 1H), 3.74 (s, 2H), 3.56 (dd, J=12.4, 7.2 Hz, 1H), 3.37 (dd, J=12.8, 5.2 Hz, 1H), 3.21 (dd, J=12.8, 3.0 Hz, 1H), 3.07 (dd, J=12.4, 5.5 Hz, 1H), 2.61-2.52 (m, 1H), 2.47-2.34 (m, 2H). $^{13}$C NMR ($D_2O$) δ 138.7, 129.5, 129.3, 127.9, 73.5, 51.5, 48.5, 45.4, 35.9, 31.8. ($MH^+$) calc for $C_{12}H_{18}NOS$: 224.1109. Found 224.1102.

Example 40

(3R,4S)-[(6-tert-Butoxy-7-benzyloxymethyl-9-deazapurin-9-yl)methyl]-3-hydroxy-(benzylthiomethyl)pyrrolidine (54). Sodium cyanoborohydride (200 mg, 3.2 mmol) was added to a stirred solution of 5 (800 mg, 2.32 mmol) and 53 (570 mg, 2.2 mmol) in methanol (10 mL) and the mixture was stirred overnight at room temperature. The crude reaction was adsorbed onto silica, dry loaded onto a silica gel flash chromatography column and eluted to afford 54 (1.10 g, 78%) as a solid. $^1$H NMR ($CDCl_3$) δ 8.45 (s, 1H), 7.62 (s, 1H), 7.27-7.22 (m, 10H), 5.75 (s, 2H), 4.51 (s, 2H), 4.15 (s, 2H), 3.67 (s, 2H), 3.38 (dd, J=10.7, 7.0 Hz, 1H), 3.12-3.02 (m, 2H), 2.69-2.63 (m, 1H), 2.54-2.49 (m, 1H), 2.44-2.39 (m, 2H), 1.70 (s, 9H). $^{13}$C NMR ($CDCl_3$) δ 156.6, 150.6, 150.0, 138.3, 137.5, 134.4, 129.3, 129.0, 128.8, 128.2, 127.8, 117.1, 109.0, 83.9, 77.9, 75.2, 70.7, 60.5, 57.7, 49.1, 47.0, 36.8, 33.7, 29.0. ($MH^+$) calc for $C_{31}H_{49}N_4O_3S$: 547.2743. Found 547.2723.

Example 41

(3R,4S)-3-Acetoxy-1-[(7-benzyloxymethyl-9-deazahypoxanthin-9-yl)methyl]-4-(benzylthiomethyl)pyrrolidine (55). Acetic anhydride (1 mL, excess) was added dropwise to a solution of 54 (1.16 g, 2.12 mmol), DMAP (30 mg, cat.), and $Et_3N$ (2 mL, excess) in $CH_2Cl_2$ (20 mL) at room temp. After 15 min. the reaction was diluted with $CH_2Cl_2$, washed with satd. $NaHCO_3$, water then brine, dried ($MgSO_4$), and concentrated in vacuo. The resulting residue was purified by flash chromatography on silica gel to afford the product (1.35 g) as a syrup. TFA (5 mL) was added dropwise to a solution of the syrup in $CH_2Cl_2$ (20 mL) at room temp. and concentrated in vacuo. The resulting residue was redissolved in $CH_2Cl_2$ and washed with satd. $NaHCO_3$ then water, dried ($MgSO_4$) and concentrated in vacuo to afford (3R,4S)-3-acetoxy-1-[(7-benzyloxymethyl-9-deazahypoxanthin-9-yl)methyl]-4-(benzylthiomethyl)pyrrolidine (55) (900 mg, 80% for two steps) as a foam. $^1$H NMR ($CDCl_3$) δ 7.90 (s, 1H), 7.33 (s, 1H), 7.28-7.17 (m; 10H), 5.91 (s, 2H), 4.85 (brs, 1H), 4.58 (s, 2H), 3.86-3.74 (m, 2H), 3.68 (s, 2H), 3.16-3.11 (m, 1H), 2.84-2.80 (m, 2H), 2.71 (dd, J=11.4, 4.6 Hz, 1H), 2.50-2.36 (m, 2H), 2.27-2.21 (m, 1H), 2.00 (s, 3H). $^{13}$C NMR ($CDCl_3$) δ 171.3, 156.2, 145.8, 141.9, 138.6, 137.5, 131.4, 129.2, 128.8, 128.3, 128.2, 127.4, 117.9, 115.2, 78.9, 77.0, 70.9, 59.8, 58.7, 48.3, 45.1, 36.9, 34.4, 21.5. HRMS ($MH^+$) calc for $C_{29}H_{33}N_4O_4S$: 533.2223. Found 533.2236.

Example 42

(3R,4S)-1-[(7-Benzyloxymethyl-9-deazaadenin-9-yl)methyl]-3-hydroxy-4-(benzylthiomethyl)pyrrolidine (56). Amine 55 (900 mg, 1.7 mmol) was dissolved in $POCl_3$ (15 mL) and heated at reflux for 1 h. The resulting solution was concentrated in vacuo and codistilled with toluene (×2) to afford a solid residue. Without further purification this residue was redissolved in 7 N $NH_3$ in MeOH (15 mL) and heated in a sealed tube at 130° C. overnight. The reaction was concentrated in vacuo and the resulting residue purified by flash chromatography on silica gel to afford (3R,4S)-1-[(7-benzyloxymethyl-9-deazaadenin-9-yl)methyl]-3-hydroxy-4-(benzylthiomethyl)pyrrolidine (56) (720 mg, 87% yield for two steps) as a syrup. $^1$H NMR ($CDCl_3$) δ 8.32 (s, 1H), 7.67 (s, 1H), 7.35-7.25 (m, 10H), 5.52 (s, 2H), 4.56 (s, 2H), 4.23 (s, 2H), 3.68 (s, 2H), 3.54-3.48 (m, 1H), 3.22 (d, J=3.4 Hz, 2H), 2.83 (brs, 1H), 2.63-2.45 (m, 4H). $^{13}$C NMR ($CDCl_3$) δ 152.2, 151.6, 149.5, 138.2, 135.7, 134.5, 129.2, 129.1, 128.9, 128.8, 128.2, 127.5, 115.2, 107.4, 77.6, 74.9, 70.7, 60.2, 57.3, 48.5, 46.9, 46.3, 36.7, 33.5, 23.1.

Example 43

(3R,4S)-1-[(9-Deazaadenin-9-yl)methyl]-3-hydroxy-4-(benzylthiomethyl)pyrrolidine (57). Amine 56 (330 mg, 0.7 mmol) was dissolved in a solution of MeOH (4 mL) and cHCl (4 mL) and heated under reflux for 90 min. The reaction was cooled to room temperature, diluted with water (50 mL), washed with $CHCl_3$ (×2), and the aqueous layer concentrated in vacuo, followed by codistillation with water (×2). The resulting residue was redissolved in $NH_4OH$, concentrated in vacuo, and the residue purified by flash chromatography on silica gel to afford (3R,4S)-1-[(9-deazaadenin-9-yl)methyl]-3-hydroxy-4-(benzylthiomethyl)pyrrolidine (57) (30 mg, 12%) as a solid. $^1$H NMR ($d_4$-MeOH) δ 8.17 (s, 1H), 7.46 (s, 1H), 7.26-7.16 (m, 5H), 3.93-3.90 (m, 1H), 3.83-3.74 (m, 2H), 3.68 (s, 2H), 3.03-2.97 (m, 1H), 2.80 (dd, J=10.2, 6.4 Hz, 1H), 2.66-2.58 (m, 2H), 2.38 (dd, J=12.5, 8.9 Hz, 1H), 2.30 (dd, J=9.5, 7.2 Hz, 1H), 2.20-2.14 (m, 1H). $^{13}$C NMR ($d_4$-MeOH) δ 152.5, 151.4, 147.4, 140.4, 130.4, 130.4, 129.8, 128.3, 115.5, 112.9, 77.3, 62.7, 59.2, 49.3, 48.6, 37.5, 35.6. HRMS ($MH^+$) calc for $C_{19}H_{24}N_6OS$: 370.1702. Found 370.1694.

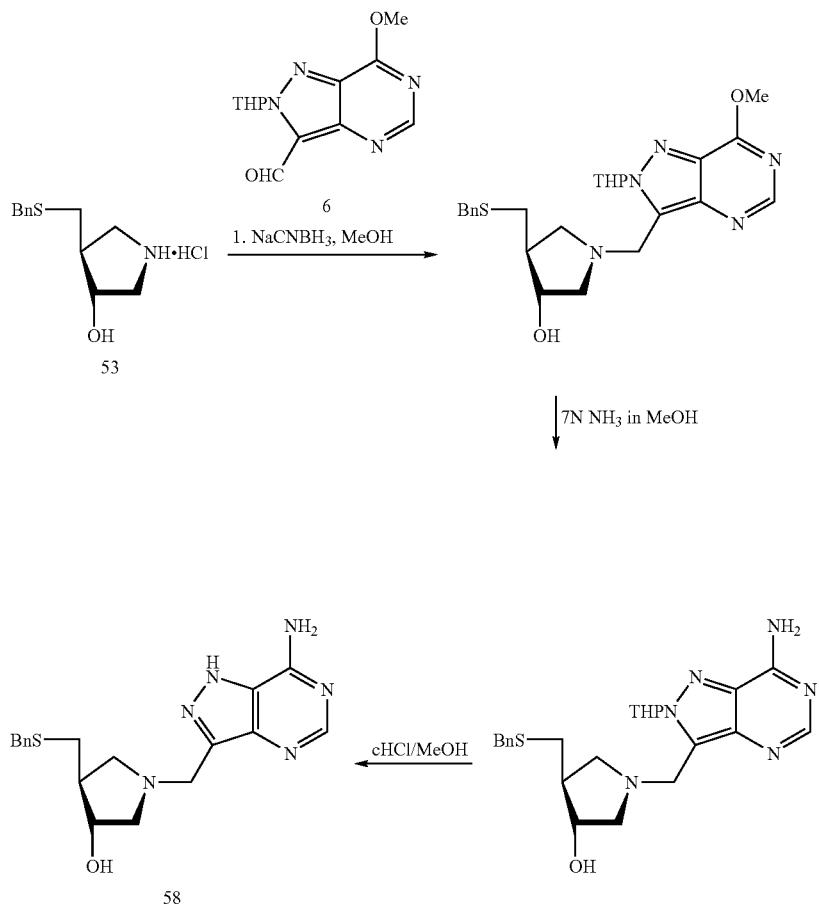

Example 44

(3R,4S)-1-[(8-Aza-9-deazaadenin-9-yl)methyl]-3-hydroxy-4-(benzylthiomethyl)pyrrolidine hydrochloride (58). Sodium cyanoborohydride (20 mg, 0.32 mmol) was added to a stirred solution of 6 (180 mg, 0.52 mmol) and (3R,4S)-3-hydroxy-(benzylthiomethyl)pyrrolidine hydrochloride (53) (95 mg, 0.37 mmol) in methanol (5 mL) and stirred overnight at room temp. The crude reaction was adsorbed onto silica, dry loaded onto a silica gel flash chromatography column and eluted to afford (3R,4S)-{[8-aza-deaza-8-(tetrahydropyran-2-yl)-6-methoxyhypoxanthin-9-yl]methyl}-3-hydroxy-4-(benzylthiomethyl)pyrrolidine (80 mg, 46%) as a foam. This was redissolved in 7 N $NH_3$ in MeOH (15 mL) and heated in a sealed tube at 110° C. overnight. The reaction was concentrated in vacuo and the resulting residue purified by flash chromatography on silica gel to afford (3R,4S)-1-{[8-aza-9-deaza-8-(tetrahydropyran-2-yl)-adenin-9-yl]methyl}-3-hydroxy-4-(benzylthiomethyl)pyrrolidine. The product was not characterized but redissolved in methanol (2.0 mL) and cHCl (2 mL), concentrated in vacuo and the resulting residue triturated with isopropanol to afford (3R,4S)-1-[(8-aza-9-deazaadenin-9-yl)methyl]-3-hydroxy-4-(benzylthiomethyl)pyrrolidine hydrochloride (58) (52 mg, 82%) as a white solid. $^{13}$C NMR ($d_4$-MeOH) δ 153.7, 152.0, 139.9, 138.8, 135.1, 130.4, 130.0, 128.5, 74.6, 61.4, 58.4, 50.4, 47.7, 37.4, 33.4. (MH$^+$) calc for $C_{18}H_{23}N_6OS$: 371.1654. Found 371.1670.

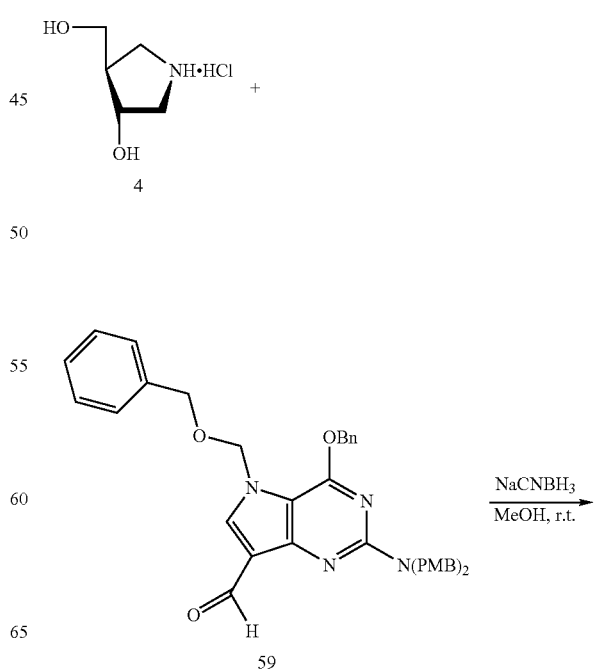

Scheme 16

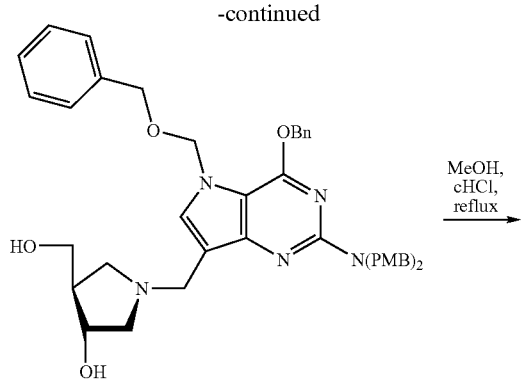

60

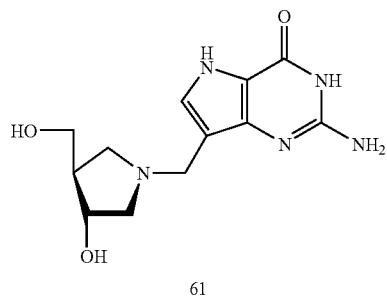

61

Example 45

7-Benzyloxymethyl-6-O-benzyl-9-deaza-9-formyl-$N^2$,$N^2$-bis(4-methoxybenzyl)guanine (59). n-Butyllithium (0.5 mL, 1.5 M) was added dropwise to a stirred solution of 7-benzyloxymethyl-6-benzyl-9-bromo-deaza-$N^2$,$N^2$-bis(4-methoxybenzyl)-guanine (Evans, G. B.; Furneaux, R. H.; Hausler, H.; Larsen, J. S.; Tyler, P. C. manuscript in preparation) in diethyl ether (6 mL) and anisole (3 mL) at −80° C. under an inert atmosphere. The reaction was stirred for an additional 30 min at −80° C. and then DMF (1.0 mL) was added and the reaction was allowed to warm to room temp. The reaction was quenched with water (50 mL) and extracted with chloroform (2×100 mL). The organic layers were combined, washed with brine, dried (MgSO$_4$), filtered and concentrated in vacuo to afford a solid residue. The solid was triturated with ethanol to afford 59 (280 mg, 72%) as a white solid. M.p. 172-174° C. $^1$H NMR δ 10.25 (s, 1H), 7.79 (s, 1H), 7.30-7.21 (m, 13H), 6.85-6.82 (m, 5H), 5.62 (s, 2H), 5.44 (s, 2H), 4.84 (s, 4H), 4.45 (s, 2H), 3.79 (s, 6H). $^{13}$C NMR δ 185.5, 159.4, 159.1, 156.5, 153.9, 136.9, 136.7, 134.9, 131.5, 129.5, 128.9, 128.5, 128.3, 128.0, 117.3, 114.2, 111.0, 78.4, 71.0, 67.9, 55.7, 49.5. HRMS (MH$^+$) calc. for $C_{38}H_{37}N_4O_5$: 629.2764. Found 629.2749.

Example 46

(3R,4R)-1-{[6-O-Benzyl-7-benzyloxymethyl-9-deaza-$N^2$,$N^2$-bis(4-methoxybenzyl)guanin-9-yl]methyl}-3-hydroxy-4-hydroxymethylpyrrolidine (60). Sodium cyanoborohydride (200 mg, 3.0 mmol) was added to a stirred solution of 59 (530 mg, 0.84 mmol) and 4.HCl (163 mg, 1.06 mmol) in methanol (10 mL) and the mixture was then stirred overnight at room temperature. The reaction mixture was absorbed onto silica and concentrated in vacuo. Chromatography of the resulting residue afforded 60 (430 mg, 70%) as a white solid. M.p. 98-100° C. $^1$H NMR δ 7.49 (s, 1H), 7.35- 7.12 (s, 14H), 6.81 (d, J=8.5 Hz, 4H), 5.59 (s, 2H), 5.47 (s, 2H), 4.85-4.73 (m, 4H), 4.44 (s, 2H), 4.23-4.12 (m, 3H), 3.75 (s, 6H), 3.50-3.35 (m, 3H), 3.20 (dd, J=12.0, 5.0 Hz, 1H), 3.08 (d, J=12.0 Hz, 1H), 2.95 (dd, J=11.4, 5.4 Hz, 1H), 2.24 (brs, 1H). $^{13}$C NMR δ 159.0, 158.4, 156.7, 153.1, 137.6, 137.0, 135.0, 131.5, 129.4, 128.9, 128.7, 128.4, 128.3, 128.1, 128.0, 125.7, 114.3, 110.6, 105.1, 78.1, 73.1, 70.8, 68.0, 62.2, 60.7, 55.7, 54.8, 49.2, 48.9. HRMS (MH$^+$) calc for $C_{43}H_{48}N_5O_6$: 730.3605. Found 730.3629.

Example 47

(3R,4R)-1-[(9-Deazaguanin-9-yl)methyl]-3-hydroxy-4-(hydroxymethyl)pyrrolidine (61). cHCl (2 mL) was added dropwise to a solution of 60 (370 mg, 0.5 mmol) in methanol (4 mL) and the resulting solution heated under reflux for 4 h. The reaction was cooled to room temp. and then concentrated in vacuo. The resulting residue was partitioned between water and chloroform, separated and the water layer concentrated in vacuo. Silica gel and ion exchange chromatography of the resulting residue afforded 61 (39 mg, 28%) as a white solid. M.p. 223-225° C. $^1$H NMR δ 7.18 (s, 1H), 4.03-3.98 (m, 1H), 3.58 (s, 2H), 3.55 (dd, J=11.1, 6.3 Hz, 1H), 3.45 (dd, J=11.1, 7.4 Hz, 1H), 2.97 (dd, J=10.0, 8.5 Hz, 1H), 2.79 (dd, J=10.9, 6.3 Hz, 1H), 2.64 (dd, J=10.9, 4.0 Hz, 1H), 2.35 (dd, J=10.3, 7.0 Hz, 1H), 2.20-2.09 (m, 1H). $^{13}$C NMR δ 158.6, 152.8, 143.5, 129.6, 112.7, 107.9, 72.8, 62.6, 60.2, 54.8, 48.9, 47.8. HRMS (MH$^+$) calc for $C_{12}H_{10}N_5O_3$: 280.1410. Found 280.1413. Anal. ($C_{12}H_{17}N_6O_3$·½H$_2$O) C, H, N.

Example 48

Mannich Reaction—General Procedure

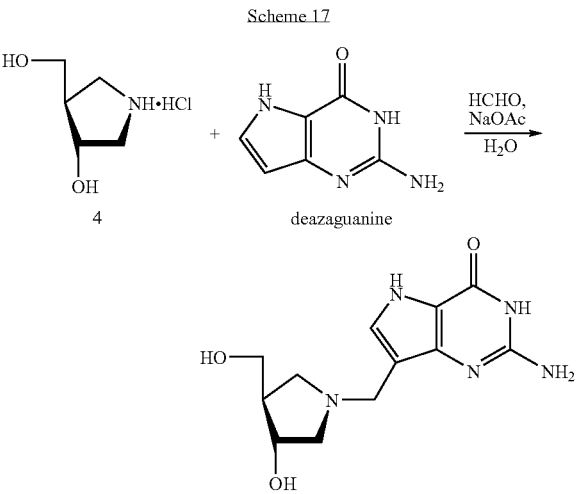

Example 48.1

General Procedure (3R,4R)-1-[(9-Deazaguanin-9-yl)methyl]-3-hydroxy-4-hydroxymethylpyrrolidine (61). (3R,4R)-3-Hydroxy 4-(hydroxymethyl)pyrrolidine hydrochloride (4) (154 mg, 1.0 mmol) and sodium acetate (82 mg, 1.0 mmol) were dissolved in water (2 mL) and to the solution were added aqueous formaldehyde (82 μL, 1.0 mmol) and deazaguanine (120 mg, 0.8 mmol). The reaction was stirred at 95° C. for 12 h. Silica gel (1.0 g) was added and the mixture was evaporated to dryness. Purification by chromatography on silica gel, using $CH_2Cl_2$:MeOH:$NH_4OH$ (5:4:1) as the eluent, afforded n as the acetic acid salt. After conversion to the HCl salt and $^1H$ and $^{13}C$ NMR spectra analysis, the compound was found to be identical in all respects with that previously reported (Evans, G. B.; Furneaux, R. H.; Lewandowicz, A.; Schramm, V. L.; Tyler, P. C. *J. Med. Chem.*, in press.)

Table: Further Compounds Prepared Via the Mannich Reaction General Procedure

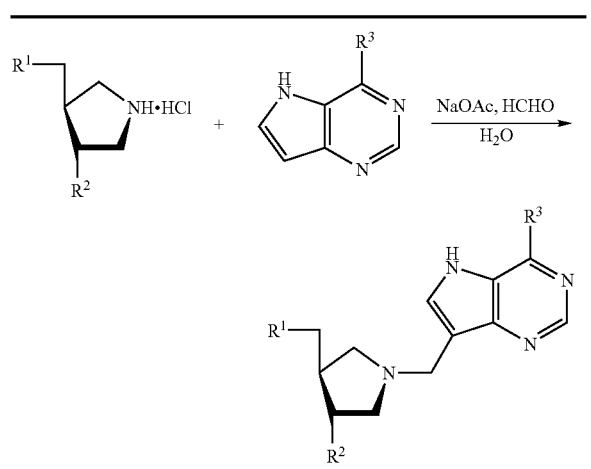

| compound | time (h) | R¹ | R² | R³ | yield (%) |
|---|---|---|---|---|---|
| 8 | 16 | OH | OH | OH | 47 |
| 10 | 1 | OH | OH | $NH_2$ | 65 |
| 57 | 1 | SBn | OH | $NH_2$ | 72 |
| 62 | 1 | SPhpCl | OH | $NH_2$ | 72 |
| 63 | 3 | OH | OH | Cl | 78 |
| 64 | 3 | OH | OH | $N_3$ | 65 |
| 65 | 1 | OAc | OAc | $NH_2$ | 49 |

Example 48.2

(3R,4R)-1-[(9-Deazahypoxanthin-9-yl)methyl]-3-hydroxy-4-hydroxymethylpyrrolidine (8). The Mannich reaction general procedure (above) was followed to afford compound 8 as the acetic acid salt. After conversion to the HCl salt and $^1H$ and $^{13}C$ NMR spectra analysis, the compound was found to be identical in all respects with that previously reported. (Evans, G. B.; Furneaux, R. H.; Lewandowicz, A.; Schramm, V. L.; Tyler, P. C. *J. Med. Chem.*, in press.)

Example 48.3

(3R,4R)-1-[(9-Deazaadenin-9-yl)methyl]-3-hydroxy (hydroxymethyl)pyrrolidine (10). The Mannich reaction general procedure (above) was followed to afford compound 10 as the acetic acid salt. $^1H$ NMR ($d_4$-MeOH) δ 8.20 (s, 1H), 7.65 (s, 1H), 4.27 (s, 1H), 4.22 (quintet, J=3.0 Hz, 1H), 3.59 (m, 2H), 3.46 (dd, J=11.1, 8.3 Hz, 1H), 3.26 (dd, J=11.4, 5.7 Hz, 1H), 3.11 (dd, J=11.4, 3.0 Hz, 1H), 2.95 (dd, J=11.2, 6.8 Hz, 1H), 2.37 (brs, 1H), 1.82 (s, 3H). $^{13}C$ NMR ($d_4$-MeOH) 152.9, 151.9, 147.1, 132.0, 115.8, 108.2, 73.6, 63.1, 61.9, 56.0, 50.8, 49.5, 23.7. HRMS (MH⁺) calc for $C_{12}H_{18}N_5O_2$: 264.1461. Found 264.1457.

Example 48.4

(3R,4S)-1-[(9-Deazaadenin-9-yl)methyl]-3-hydroxy-4-(benzylthiomethyl)pyrrolidine (57). The Mannich reaction general procedure (above) was followed to afford compound 57 as the acetic acid salt. The acetic acid salt was converted to the free base via ion exchange chromatography. $^1H$ NMR ($d_4$-MeOH) 8.17 (s, 1H), 7.46 (s, 1H), 7.26-7.16 (m, 5H), 3.93-3.90 (m, 1H), 3.83-3.74 (m, 2H), 3.68 (s, 2H), 3.03-2.97 (m, 1H), 2.80 (dd, J=10.2, 6.4 Hz, 1H), 2.66-2.58 (m, 2H), 2.38 (dd, J=12.5, 8.9 Hz, 1H), 2.30 (dd, J=9.5, 7.2 Hz, 1H), 2.20-2.14 (m, 1H). $^{13}C$ NMR ($d_4$-MeOH) 152.5, 151.4, 147.4, 140.4, 130.4, 130.4, 129.8, 115.5, 112.9, 77.3, 62.7, 59.2, 49.3, 48.6, 37.5, 35.6. HRMS (MH⁺) calc for $C_{19}H_{24}N_5OS$: 370.1702. Found 370.1694.

Example 48.5

(3R,4S)-1-[(9-Deazaadenin-9-yl)methyl]-3-hydroxy-4-(4-chlorophenylthiomethyl)pyrrolidine (62). The Mannich reaction general procedure (above) was followed to afford compound 62 as the acetic acid salt. $^1H$ NMR ($d_4$-MeOH) 8.25 (s, 1H), 7.84 (s, 1H), 7.35-7.23 (m, 5H), 4.54 (s, 2H), 4.30 (m, 1H), 3.74 (dd, J=11.9, 7.9 Hz, 1H), 3.59 (dd, J=12.2, 5.6 Hz, 1H), 3.40-3.15 (m, 4H), 2.89 (dd, J=13.5, 9.1 Hz, 1H), 2.47 (brs, 1H), 1.98 (s, 3H). $^{13}C$ NMR ($d_4$-MeOH) 153.0, 151.8, 146.1, 135.7, 134.0, 133.2, 132.2, 130.7, 115.7, 105.5, 74.6, 60.4, 57.3, 49.2, 47.7, 36.1, 23.0. HRMS (MH⁺) calc for $C_{18}H_{21}ClN_5OS$: 390.1155. Found 390.1264.

Example 48.6

(3R,4R)-1-[(6-Chloro-9-deazapurin-9-yl)methyl]-3-hydroxy (hydroxymethyl)pyrrolidine (63). The Mannich reaction general procedure (above) was followed to afford compound 63 as the acetic acid salt. $^1H$ NMR ($D_2O$) 8.34 (s, 1H), 7.98 (s, 1H), 4.48 (s, 2H), 4.31 (m, 1H), 3.68 (dd, J=12.1, 8.3 Hz, 1H), 3.53 (d, J=5.9 Hz, 2H), 3.45 (dd, J=12.6, 5.5 Hz, 1H), 3.32 (dd, J=12.6, 2.5 Hz, 1H), 3.13 (dd, J=12.0, 7.4 Hz, 1H), 2.40 (brs, 1H), 1.82 (s, 3H). $^{13}C$ NMR ($d_4$-MeOH) 149.7, 148.6, 143.4, 137.6, 124.8, 104.5, 71.3, 60.7, 59.8, 54.4, 48.0, 47.8, 23.5. HRMS (MH⁺) calc for $C_{12}H_{16}ClN_4O_2$: 283.0962. Found 283.0973.

Example 48.7

(3R,4R)-1-[(6-Azido-9-deazapurin-9-yl)methyl]-3-hydroxy-4-(hydroxymethyl)pyrrolidine (64). The Mannich reaction general procedure (above) was followed to afford compound 64 as the acetic acid salt. $^1H$ NMR ($D_2O$) 9.52 (s, 1H), 7.89 (s, 1H), 4.62 (s, 2H), 4.38 (m, 1H), 3.78 (dd, J=12.0, 8.5 Hz, 1H), 3.60 (d, J=5.9 Hz, 2H), 3.55 (t, J=5.5 Hz, 1H), 3.42 (brd, J=11.4 Hz, 1H), 3.23 (dd, J=11.9, 7.3 Hz, 1H), 2.48 (brs, 1H), 1.86 (s, 3H). $^{13}C$ NMR ($D_2O$) 141.7, 138.6, 133.6, 132.2, 111.7, 107.2, 71.4, 60.8, 59.9, 54.6, 48.0, 48.0, 23.7.

Example 48.8

(3R,4R)-1-[(9-Deazaadenin-9-yl)methyl]-3-acetoxy-4-(acetoxymethyl)pyrrolidine (65). The Mannich reaction general procedure (above) was followed to afford compound 65 as the acetic acid salt. $^1H$ NMR ($D_2O$) 8.25 (s, 1H), 7.69 (s, 1H), 5.05 (quintet, J=2.8 Hz, 1H), 4.23-4.06 (m, 4H), 3.40 (dd, J=10.5, 8.1 Hz, 1H), 3.27-3.12 (m, 2H), 2.77 (dd, J=10.5, 7.8 Hz, 1H), 2.63 (m, 1H), 2.03 (s, 3H), 2.00 (s, 3H), 1.98 (s, 3H). $^{13}C$ NMR ($D_2O$) 172.9, 172.6, 153.0, 151.1, 145.4, 132.1, 115.6, 108.8, 76.6, 65.1, 59.6, 55.8, 48.6, 45.7, 23.4, 21.3, 21.1. HRMS (MH+) calc for $C_{16}H_{22}N_5O_4$: 348.1672. Found 348.1669.

Example 49

Inhibition of PNP

The reaction involves the conversion of inosine (1 mM) and inorganic phosphate (50 mM, pH 7.4) to hypoxanthine and α-D-ribose 1-phosphate. Analysis by this method requires that the inhibitor concentration be present at least 10× the enzyme concentration. Enzyme was present at 1.6 pM. The reaction progress was followed in a coupled assay by monitoring the formation of uric acid from oxidation of hypoxanthine by xanthine oxidase (128 μg; 59 munits/ml reaction mixture). The inhibitor concentration from 0 to 1 nM was used to determine the initial dissociation constant. $K_i$ was determined from the time interval of 0 to 4 min and the equilibrium dissociation constant $K_i^*$ was determined from the time interval from 35 to 45 min. Inhibition constants ($K_i$ or $K_i^*$) were determined according to the equations $v=(k_{cat})(A)/(K_m \cdot (1+I/K_i)+A)$ for $K_i$ or $v=(k_{cat})(A)/(K_m \cdot (1+I/K_i^*)+A)$ for $K_i^*$.

The kinetic curves for human PNP inhibited by compound (8) are shown in FIG. 1; the concentration of inhibitor is indicated on the right hand side.

Example 50

Inhibition of MTAP and MTAN

Continuous spectrophotometric assays as well as discontinuous assays were used to characterize the inhibitors of the invention and in vivo inhibition of MTAP and/or MTAN. In the continuous spectrophotometric assays the conversion of MTA into adenine was measured as a decrease in absorbance at 274 nm. At 274 nm, the difference in spectral properties is maximum and the millimolar extinction coefficient ($cm^{-1}$) is 1.6 for the conversion of MTA to adenine. In the discontinuous assay, mixtures of 10 to 20 μL containing 50 μM [2,8-$^3$H] MTA (285 cpm/pmol) in 50 mM potassium phosphate buffer pH 7.5, 10 mM KCl and enzyme were incubated at room temperature. The reactions were stopped by the addition of 1 μL of concentrated HCl or 60% perchloric acid. Adenine was added as a carrier (1 to 2 μL of 6 mM) and samples of 5 μL were spotted onto thin layer cellulose sheets and developed in 1M ammonium acetate pH 7.55 and isopropanol at a ratio of 9:1. Following development, adenine spots were located by ultraviolet light absorbance, excised and counted for the content of tritium. For analysis of MTAP activity in blood samples, 6 μL of a mixture containing 1:1 blood:0.6% Triton X-100 was added to the assay mixture described above and samples taken at appropriate times for analysis by thin layer chromatography. Assays for MTAP activity from mouse liver were accomplished in a similar manner. Liver extracts (3 μL) containing approximately 100 μg of protein were added to the assay mixtures for appropriate times followed by analysis by thin layer chromatography.

Slow-Onset Inhibition and Inhibition Constants

The kinetics for slow onset inhibition and the measurement of $K_i$ and $K_i^*$ values were carried out by adding enzyme of known concentrations (1 to 5 nM) to reaction mixtures having high concentrations of substrate and various concentrations of inhibitors. Substrate concentrations of 150 μM were typically used for MTA nucleosidase and 200 μM for MTA phosphorylase. These concentrations correspond to an OD between 0.7 and 1.1 at 274 nM. The formation of product is monitored as a decrease in absorbance at 274 nm. Conditions for $K_i^*$ determination used high concentration of substrate. Two controls, one having no inhibitor and other no enzyme were included in the experiment. The $K_i$ values of these enzymes for the inhibitors were calculated by fitting in the ratio of initial rates in the presence of inhibitor to those without inhibitor versus the inhibitor concentration, for the known $K_m$ and substrate concentration into the following expression:

$$\frac{V_o'}{V_o} = \frac{K_m + [S]}{K_m + [S] + \frac{K_m[I]}{K_i}}$$

Where
$V_o'$ is the rate in the presence of inhibitor
$V_o$ rate in the absence of inhibitor
[I] inhibitor concentration
And [S] is the substrate concentration And the $K_i^*$ was calculated by fitting to following expression $$\frac{V_s'}{V_s} = \frac{K_m + [S]}{K_m + [S] + \frac{K_m[I]}{K_i^*}}$$

Where $V_s'$ is the steady-state rate following attainment of equilibrium in the presence inhibitor, and $V_s$ is the steady-state rate in the control having no inhibitor. These equations describe competitive inhibition where substrate and transition state analogue inhibitor bind in a mutually exclusive manner to the enzyme.

Example 51

Inhibition of Mouse MTAP In Vivo

Figure 2:
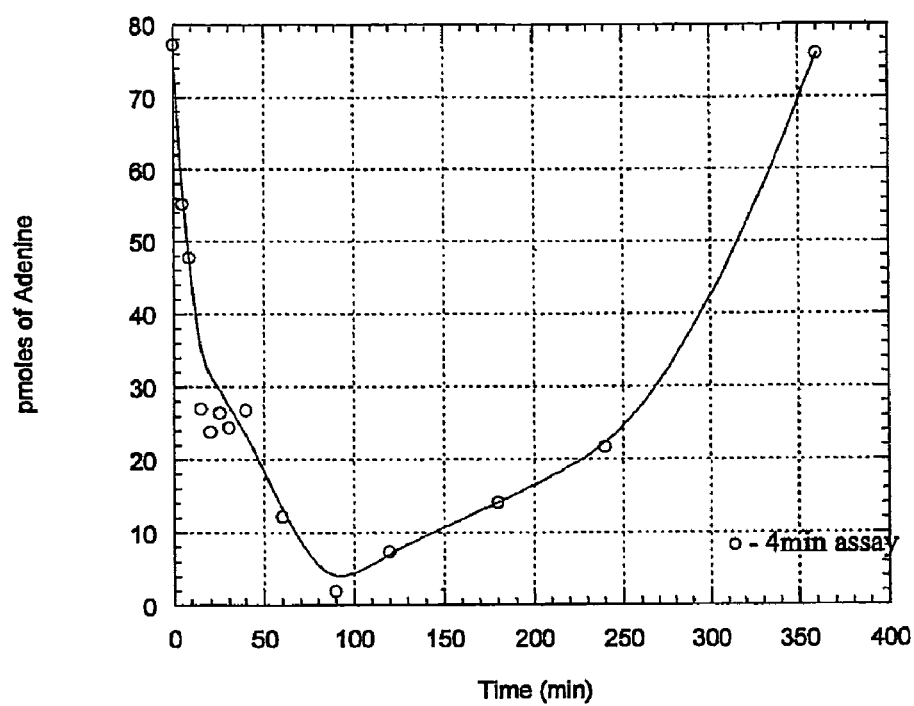
FIG. 2 shows in vivo inhibition of mouse MTAP.

A mouse was fed 200 micrograms of Compound 57, and samples of blood were taken as a function of time. Cells were lysed and assayed for residual MTAP activity in assay mixtures containing MTA. The assay measures the release of adenine from [2,8-$^3$H]MTA. The results are shown in FIG. 2.

Although the invention has been described by way of examples, it should be appreciated the variations or modifications may be made without departing from the scope of the invention. Furthermore, when known equivalents exist to specific features, such equivalents are incorporated as if specifically referred to in the specification.

INDUSTRIAL APPLICABILITY

The present invention relates to compounds that are inhibitors of PNP, PPRT, MTAP, MTAN and/or NH. The compounds are therefore expected to be useful in the treatment of diseases in which the inhibition of PNP, PPRT, MTAP, MTAN and/or NH is desirable. Such diseases include cancer, bacterial infection, protozoal infection or T-cell mediated diseases.

The invention claimed is:

1. A compound of the formula (I):

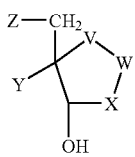

wherein:
V is selected from $CH_2$ and NH, and W is $NR^1$; or V is $NR^1$, and W is selected from $CH_2$ and NH;
X is selected from $CH_2$ and CHOH in the R or S-configuration;
Y is selected from hydrogen, halogen and hydroxy, except where V is selected from NH and $NR^1$, then Y is hydrogen;
Z is selected from hydrogen, halogen, hydroxy, SQ, OQ and Q, where Q is an alkyl, aralkyl or aryl group;
$R^1$ is a radical of the formula (II)

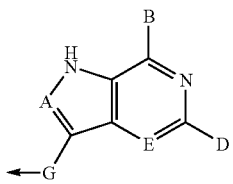

A is N;
B is selected from OH, $NH_2$, $NHR^6$, SH, hydrogen and halogen, where $R^6$ is an alkyl, aralkyl or aryl group;
D is selected from OH, $NH_2$, $NHR^7$, hydrogen, halogen and $SCH_3$, where $R^7$ is an alkyl, aralkyl or aryl group;
E is N;
G is selected from $CH_2$ and NH, or G is absent, provided that where W is $NR^1$ and G is NH then V is $CH_2$, and provided that where V is $NR^1$ and G is NH then W is $CH_2$,
or a tautomer thereof, or a pharmaceutically acceptable salt thereof.

2. A compound as claimed in claim 1, where Z is selected from hydrogen, halogen, hydroxy, SQ and OQ.
3. A compound as claimed in claim 1, where V is $CH_2$.
4. A compound as claimed in claim 1, where X is $CH_2$.
5. A compound as claimed in claim 1, where G is $CH_2$.
6. A compound as claimed in claim 1, where Z is OH.
7. A compound as claimed in claim 1, where Z is SQ.
8. A compound as claimed in claim 1, where Z is Q.
9. A compound as claimed in claim 1, where W is $NR^1$.
10. A compound as claimed in claim 1, where W is selected from NH and $NR^1$, and X is $CH_2$.
11. A compound as claimed in claim 1, where V, X and G are all $CH_2$, Z is OH and W is $NR^1$.
12. A compound as claimed in claim 1, where V, X and G are all $CH_2$, Z is SQ and W is $NR^1$.
13. A compound as claimed in claim 1, where Y is hydrogen.
14. A compound as claimed in claim 1, where Y is hydroxy.
15. A compound as claimed in claim 1, where B is hydroxy.
16. A compound as claimed in claim 1, where B is $NH_2$.
17. A compound as claimed in claim 1, where D is H.
18. A compound as claimed in claim 1, where D is $NH_2$.
19. A compound as claimed in claim 1, which is:
(3R,4R)-1-[(8-aza-9-deazahypoxanthin-9-yl)methyl]-3-hydroxy-4-(hydroxymethyl)pyrrolidine;
(3R,4R)-1-[(8-aza-9-deazaadenin-9-yl)methyl]-3-hydroxy-4-(hydroxymethyl)pyrrolidine;
(3R,4R)-3-hydroxy-4-hydroxymethyl-1-(hypoxanthin-9-yl)pyrrolidine; or
(3R,4S)-1-[(8-aza-9-deezaadenin-9-yl)methyl]-3-hydroxy-4-(benzylthiomethyl)pyrrolidine;
or a pharmaceutically acceptable salt thereof.

20. A pharmaceutical composition comprising a compound as claimed in claim 1 and a carrier.

* * * * *